US010564242B2

(12) United States Patent
Nagasawa et al.

(10) Patent No.: US 10,564,242 B2
(45) Date of Patent: Feb. 18, 2020

(54) SYSTEM AND METHOD FOR AUTOMATIC START TIME ADJUSTMENT IN MULTI-PHASE SCANNING

(71) Applicant: General Electric Company, Schenectady, NY (US)

(72) Inventors: Miho Nagasawa, Hino (JP); Kenji Suzuki, Hino (JP); Yoshihiro Tomoda, Hino (JP); Masanori Ozaki, Hino (JP)

(*) Notice: Subject to any disclaimer, the term of this patent is extended or adjusted under 35 U.S.C. 154(b) by 678 days.

(21) Appl. No.: 15/306,738

(22) PCT Filed: Apr. 24, 2015

(86) PCT No.: PCT/US2015/027596
§ 371 (c)(1),
(2) Date: Oct. 25, 2016

(87) PCT Pub. No.: WO2015/164788
PCT Pub. Date: Oct. 29, 2015

(65) Prior Publication Data
US 2017/0052239 A1 Feb. 23, 2017

(30) Foreign Application Priority Data
Apr. 25, 2014 (JP) .................................. 2014-091609

(51) Int. Cl.
*A61B 5/055* (2006.01)
*G01R 33/56* (2006.01)
(Continued)

(52) U.S. Cl.
CPC .......... *G01R 33/5601* (2013.01); *A61B 5/004* (2013.01); *A61B 5/055* (2013.01);
(Continued)

(58) Field of Classification Search
CPC ....... G01R 5/055; G01R 5/4244; G01R 5/004; G01R 5/007; G01R 5/5673;
(Continued)

(56) References Cited

U.S. PATENT DOCUMENTS 6,434,413 B1 * 8/2002 Liu ........................ G01R 33/56
324/307
2007/0255130 A1 11/2007 Du
2008/0310581 A1 * 12/2008 Feuerlein ............... A61B 5/055
378/4

FOREIGN PATENT DOCUMENTS

JP 2003135447 A 5/2003
JP 2004041732 A 2/2004
(Continued)

OTHER PUBLICATIONS

International Search Report and Written Opinion for International Application No. PCT/US2015/027596, dated Jul. 1, 2015, 9 pages.
(Continued)

*Primary Examiner* — Elmer M Chao

(57) ABSTRACT

An MR apparatus creating a timeline suitable for data acquisition in several temporal phases. The MR apparatus including a method for creating a timeline TL2 having a scan time of TS1 based on a reference timeline TL0 having a scan time of TS. The method setting start points in time of scans SC1, SC3 and SC4 in the timeline TL2 to the same points in time as those in the reference timeline TL0, respectively. The method also setting the start point in time of the scan SC2 in the timeline TL2 to a sum of the scan time TS1 and a delay time TD1 with respect to the scan SC1 in the timeline TL2.

13 Claims, 17 Drawing Sheets

(51) Int. Cl.
    *A61B 5/00*     (2006.01)
    *A61M 5/00*     (2006.01)
    *G01R 33/567*     (2006.01)

(52) U.S. Cl.
    CPC ........... *A61B 5/4244* (2013.01); *A61M 5/007* (2013.01); *G01R 33/5673* (2013.01)

(58) Field of Classification Search
    CPC ... G01R 33/5601; A61B 5/055; A61B 5/4244; A61B 5/004; A61B 5/007; A61B 5/5673
    See application file for complete search history.

(56) References Cited

FOREIGN PATENT DOCUMENTS

| | | | |
|---|---|---|---|
| JP | 2012075509 A | 4/2012 | |
| JP | 2013165843 A | 8/2013 | |
| JP | 2014042565 A | 3/2014 | |

OTHER PUBLICATIONS

Tada Toshifumi et al: "Diagnostic accuracy for macroscopic classification of nodular hepatocellular carcinoma: comparison of gadolinium ethoxybenzyl diethylenetriamine pentaacetic acid-enhanced magnetic resonance imaging and angiography-assisted computed tomography", Journal of Gastroenterology, Springer Japan KK, JP, vol. 50, No. 1, Feb. 22, 2014 (Feb. 22, 2014), pp. 85-94, XP035422466, ISSN: 0944-1174, DOI: 10.1007/S00535-014-0947-X [retrieved on Feb. 22, 2014] * p. 87, col. 1, lines 20-27 *.

Tada, T., et al., "Diagnostic accuracy for macroscopic classification of nodular hepatocellular carcinoma comparison of gadolinium ethoxybenzyl diethylenetriamine pentaacetic acid-enhanced magnetic resonance imaging and angiography-assisted computed tomography," Journal of Gastroenterology, vol. 50, Issue 1, pp. 85-94 (Feb. 2014).

Machine Translation and First Office Action and Search issued in connection with corresponding CN Application No. 201580022051.7 dated Aug. 27, 2018, 13 pages.

Notice of Allowance for the JP patent application No. 2014-091609, 3 pages.

* cited by examiner

FIG.17
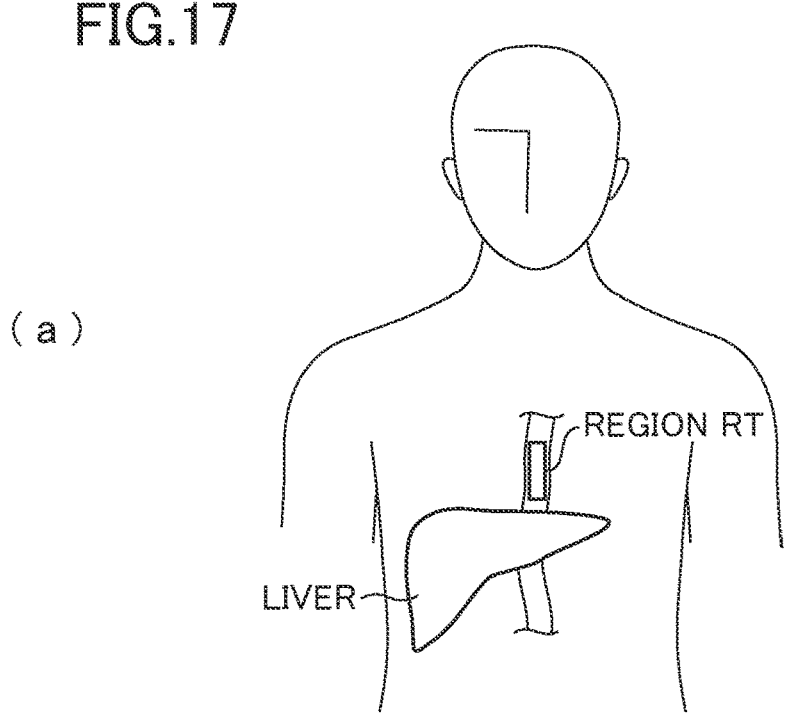
(a)
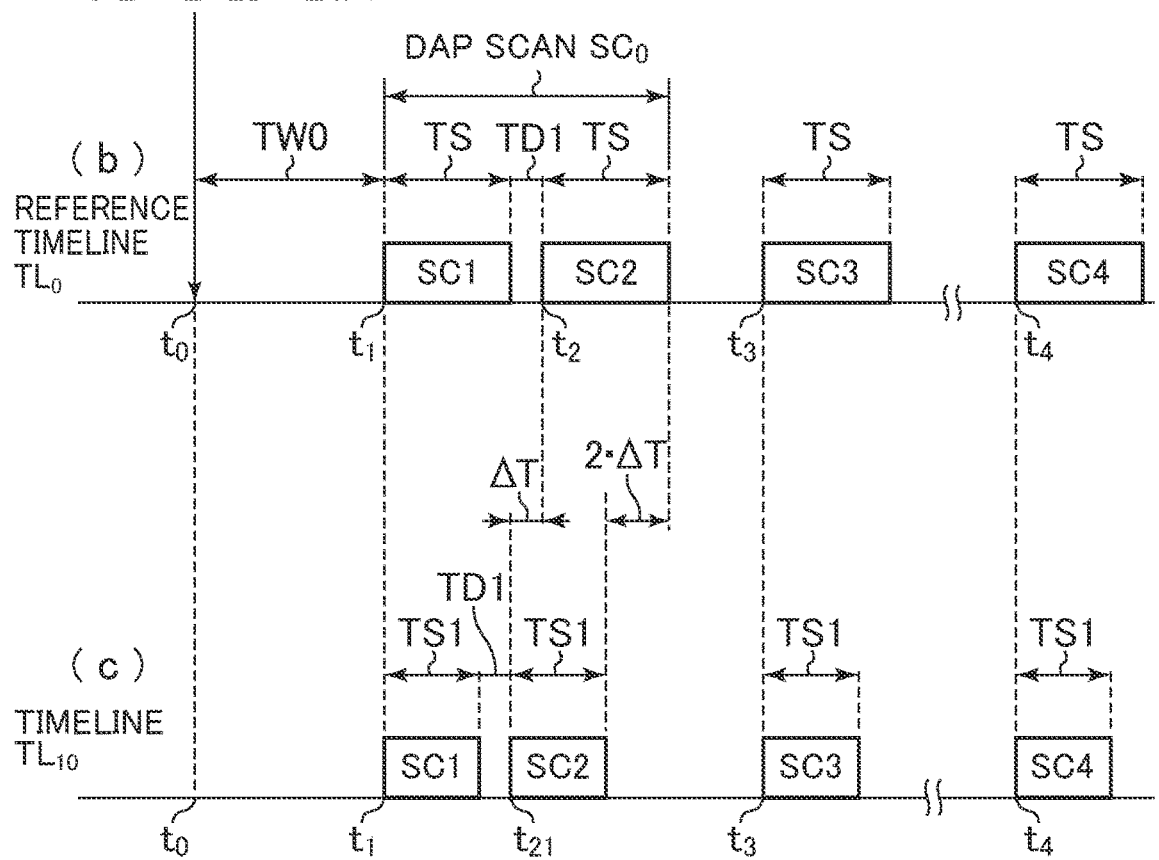
(b)

FIG.18
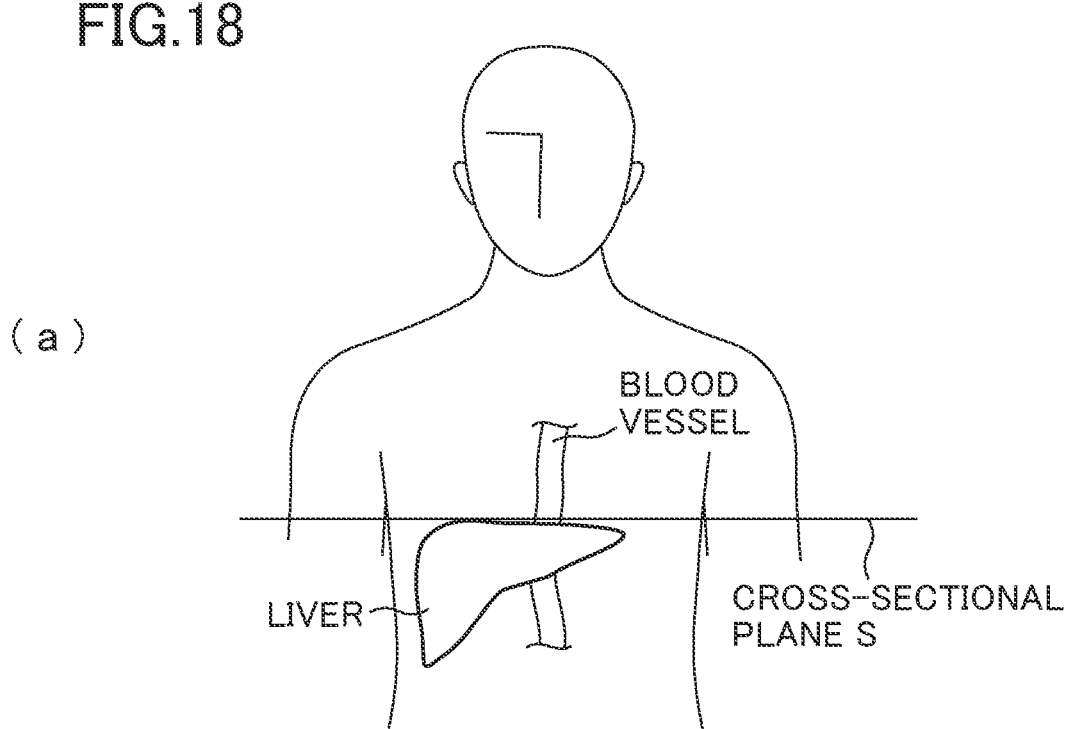
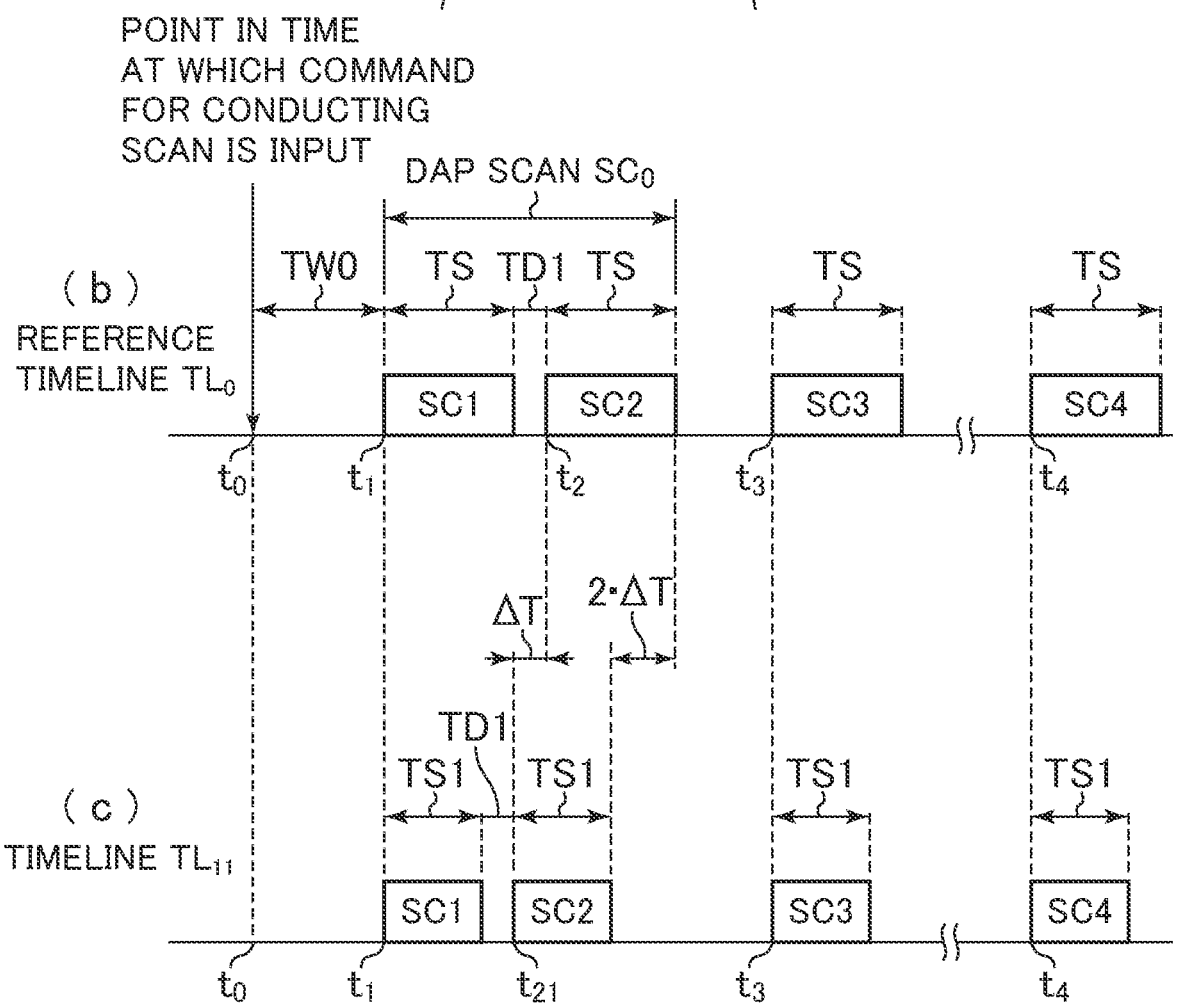

SYSTEM AND METHOD FOR AUTOMATIC START TIME ADJUSTMENT IN MULTI-PHASE SCANNING

CROSS-REFERENCE TO RELATED APPLICATIONS

This is a national stage application under 35 U.S.C. § 371(c) of PCT Patent Application No. PCT/US2015/027596, filed on Apr. 24, 2015, which claims priority to Japanese Patent Application No. 2014-091609, filed on Apr. 25, 2014, the disclosures of which are incorporated herein by reference in their entireties.

BACKGROUND

The present invention relates to a setting apparatus for setting a timeline, a medical apparatus having the setting apparatus, and a program for creating the timeline.

Known methods making diagnosis for a subject using medical apparatuses, such as magnetic resonance (MR) apparatuses, computed tomography (CT) apparatuses, and ultrasonic apparatuses, include a method of administering a contrast medium to the subject, and obtaining images in several temporal phases developed after the administration of the contrast medium.

SUMMARY

Scans for acquiring data in an arterial phase, a portal phase, and an equilibrium phase are known as a contrast examination for liver. In acquiring data in these temporal phases, a scan for acquiring data in the arterial phase, a scan for acquiring data in the portal phase, and a scan for acquiring data in the equilibrium phase are conducted. In recent years, a Double Arterial Phase scan has been made possible as a scan for acquiring data in the arterial phase. In the Double Arterial Phase scan, an early arterial phase scan for acquiring data in an early arterial phase and a late arterial phase scan for acquiring data in a late arterial phase can be conducted during a single breath-hold. Therefore, scans for acquiring data in four temporal phases, i.e., the early arterial phase, late arterial phase, portal phase, and equilibrium phase, are used in recent liver diagnosis.

In acquiring data in the four temporal phases, the scans should be conducted at times suitable for data acquisition in the respective temporal phases. Thus, the scans are generally conducted according to a timeline defining times at which data in the temporal phases are to be acquired. In the timeline are defined a start point in time representing a time at which a scan in each temporal phase is started, an interval from the end of a scan to the start of a next scan (delay time), and the like.

The scan time of each scan, however, may be long sometimes or short in the other times depending upon parameter values specified by an operator. For example, in case that the operator specifies a low resolution, the scan time is shortened, while in case that he/she specifies a high resolution, the scan time is lengthened. Since the scan time may thus take a variety of values depending upon the parameter values (for example, the number of slices, resolution) specified by the operator, the delay times and/or start points in time defined in the timeline are generally automatically modified according to the scan time.

In a multi-temporal-phase scan, however, it may be sometimes desired not to modify the delay times or start points in time regardless of the length of the scan time. For example, the interval (delay time) from the end of a scan in the early arterial phase to the start of a scan in the late arterial phase is desired to be unmodified in the Double Arterial Phase scan, and the scan start points in time are desired to be unmodified in the scans in the portal and equilibrium phases. The conventional method of modification, however, may modify the delay times and/or scan start points in time that the operator does not want to modify. In this case, the operator must manually re-modify the modified delay times and/or scan start points in time, posing a problem that workload on the operator is increased.

Thus, it is desirable to have a technique with which a timeline suitable for data acquisition in several temporal phases can be created.

A first aspect is a setting apparatus provided in a medical apparatus conducting a first scan for acquiring data in a first temporal phase from a subject to whom a contrast medium is administered, a second scan for acquiring data in a second temporal phase from said subject, and a third scan for acquiring data in a third temporal phase from said subject, said setting apparatus being for setting conditions in conducting said first, second, and third scans, said setting apparatus comprising a processor for creating a second timeline based on a first timeline, said first timeline defining a start point in time of said first scan having a first scan time, a start point in time of said second scan, a start point in time of each third scan, and a first delay time from the end of said first scan to the start of said second scan, said second timeline being a timeline in which the scan time of said first scan is modified from said first scan time to a second scan time, wherein said processor sets a second timeline based on a first timeline comprises a start point in time of said first scan in said second timeline to the same point in time as that in said first timeline; a start point in time of said second scan in said second timeline to a point in time delayed relative to the start point in time of said first scan in said second timeline by a sum of said second scan time and said first delay time; and a start point in time of said third scan in said second timeline to the same point in time as that in said first timeline.

A second aspect is a program applied to a setting apparatus provided in a medical apparatus conducting a first scan for acquiring data in a first temporal phase from a subject to whom a contrast medium is administered, a second scan for acquiring data in a second temporal phase from said subject, and a third scan for acquiring data in a third temporal phase from said subject, said setting apparatus being for setting conditions in conducting said first, second, and third scans, said program being for causing a computer to execute a creation process of creating a second timeline based on a first timeline, said first timeline defining a start point in time of said first scan having a first scan time, a start point in time of said second scan, a start point in time of each third scan, and a first delay time from the end of said first scan to the start of said second scan, said second timeline being a timeline in which the scan time of said first scan is modified from said first scan time to a second scan time, wherein said creation process sets a start point in time of said first scan in said second timeline to the same point in time as that in said first timeline: a start point in time of said second scan in said second timeline to a point in time delayed relative to the start point in time of said first scan in said second timeline by a sum of said second scan time and said first delay time: and a start point in time of said third scan in said second timeline to the same point in time as that in said first timeline.

Even in a case that the scan time is modified, a timeline suitable for data acquisition in several temporal phases can be created.

BRIEF DESCRIPTION OF THE DRAWINGS

FIG. 17 shows a diagram explaining a Fluoro trigger technique.

FIG. 18 shows a diagram explaining a Smart prep technique.

DETAILED DESCRIPTION

An embodiment of the invention will be described hereinbelow, although the present invention is not limited thereto.

Figure 1:
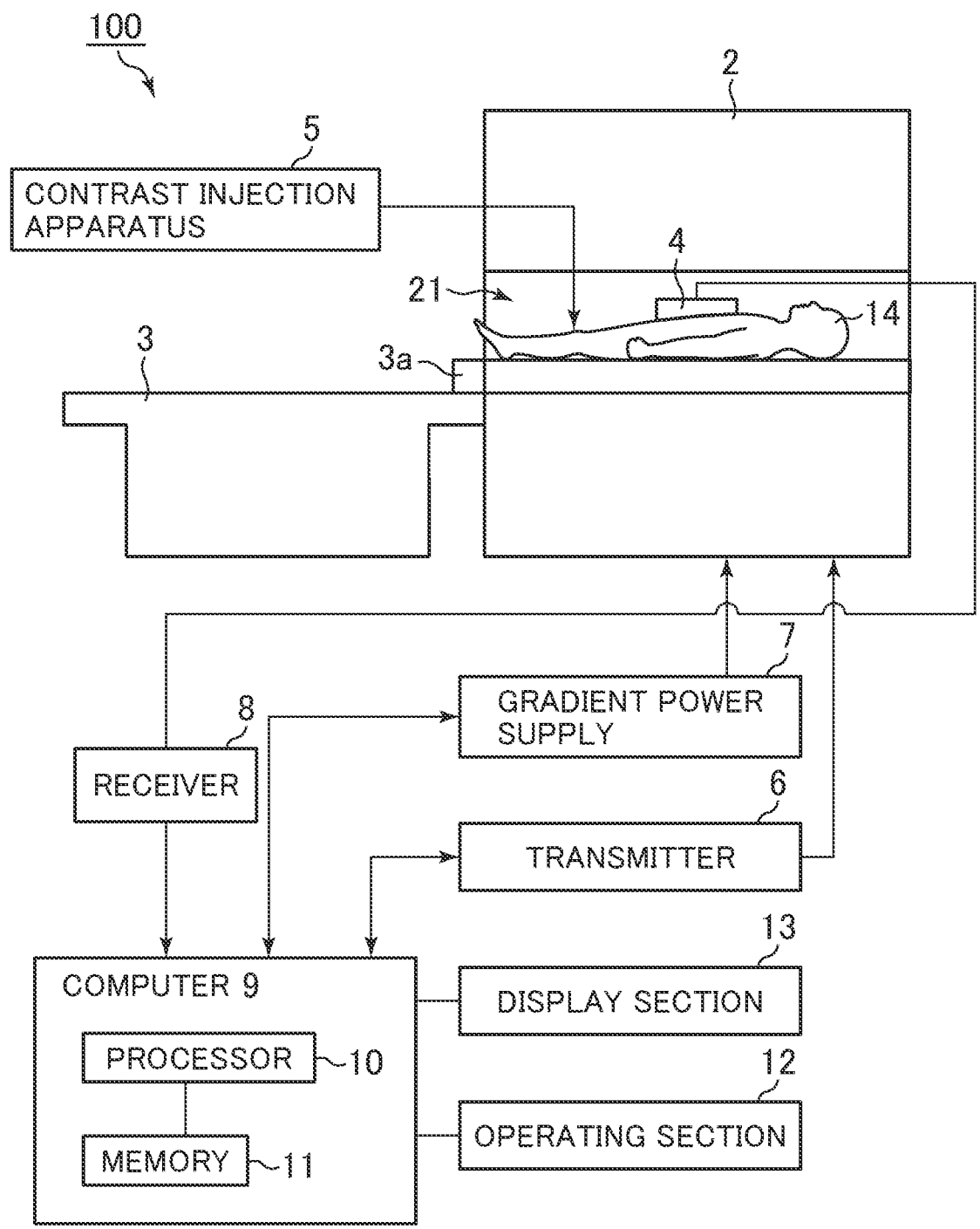
FIG. 1 shows a schematic diagram of a magnetic resonance (MR) apparatus in one embodiment of the present invention.

FIG. 1 is a schematic diagram of a magnetic resonance apparatus in one embodiment of the present invention. The magnetic resonance apparatus (referred to as "MR apparatus" hereinbelow) 100 comprises a magnet 2, a table 3, and a receiving RF coil 4.

The magnet 2 has a bore 21 into which a subject 14 is inserted. In the magnet 2 are incorporated a superconductive coil, a gradient coil, and an RF coil.

The table 3 has a cradle 3a. The cradle 3a is configured to be movable into the bore 21. The subject 14 is carried into the bore 21 by the cradle 3a.

The receiving RF coil 4 is attached to the subject 14. The receiving RF coil 4 receives magnetic resonance signals from the subject 14.

The MR apparatus 100 further comprises a contrast injection apparatus 5, a transmitter 6, a gradient power supply 7, a receiver 8, a computer 9, an operating section 12, and a display section 13.

The contrast injection apparatus 5 injects a contrast medium into the subject 14. The transmitter 6 supplies electric current to the RF coil, and the gradient power supply 7 supplies electric current to the gradient coil. The receiver 8 applies signal processing such as detection/demodulation to signals received from the receiving RF coil 4.

The computer 9 controls operations of several sections in the MR apparatus 100 to implement several kinds of operation of the MR apparatus 100, including an operation of transmitting required information to the display section 13, an operation of reconstructing an image, etc. The computer 9 comprises a processor 10 and memory 11.

Figure 2:
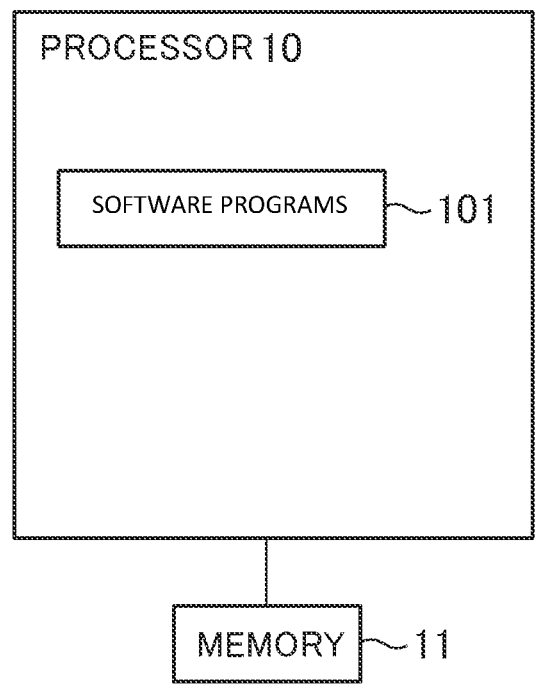
FIG. 2 shows a diagram showing processing executed by a processor 10.

The memory 11 stores therein programs executed by the processor 10, a reference timeline (see FIG. 5), which will be discussed later. The processor 10 loads thereon a program stored in the memory 11, and executes processing written in the program. FIG. 2 shows processing executed by the processor 10. The processor 10 includes software programs stored in the memory 11. The software programs 101 create a timeline defining a start point in time of each scan.

The processor 10 functions by executing the software programs 101 stored in memory 11.

The operating section 12 is operated by an operator to input several kinds of information to the computer 9. The display section 13 displays several kinds of information. The MR apparatus 100 is constructed as described above.

In the present embodiment, the MR apparatus 100 is used to conduct a localizer scan and a main scan. The localizer scan is a scan for obtaining an image for use in setting slices, etc. In the localizer scan, an axial image, a sagittal image, and a coronal image are obtained, for example. In the main scan, imaging using a contrast medium is conducted (see FIG. 3).

Figure 3:
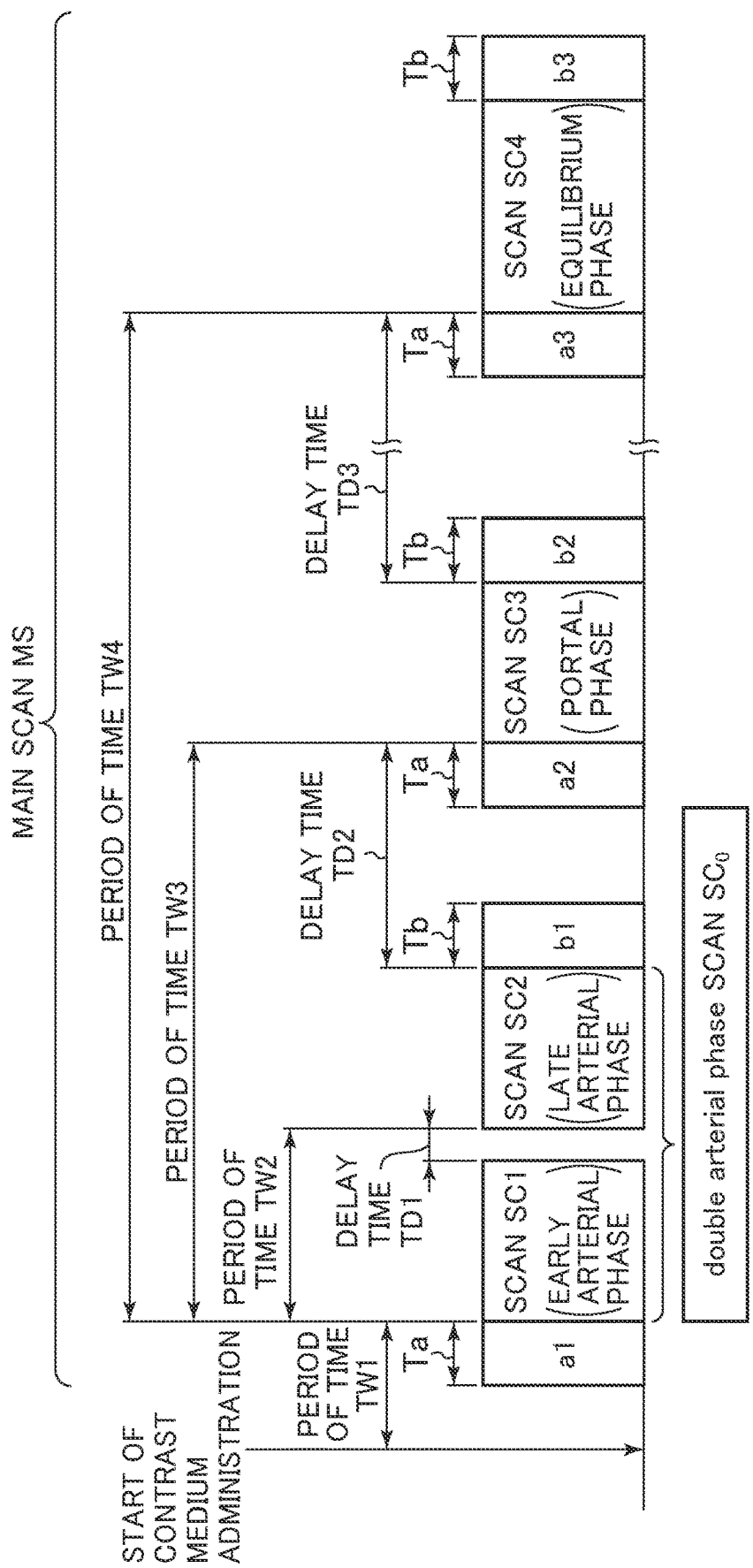
FIG. 3 shows a diagram explaining a main scan MS.

FIG. 3 is a diagram explaining the main scan. In the main scan MS, a contrast medium is administered. After the contrast medium is administered, a scan is conducted.

In the main scan MS, a Double Arterial Phase scan (referred to as "DAP scan" hereinbelow) SC0 is first conducted, wherein double imaging of arterial phase is conducted during a subject's breath-hold. The DAP scan SC0 is started at a point in time after a period of time TW1 has elapsed from the start of contrast medium administration. The period of time TW1 is set to a value ranging from 10 to 15 seconds, for example. The DAP scan SC0 is conducted during a subject's breath-hold. Therefore, before the DAP scan SC0 is started, a breath-hold message a1 for asking the subject to hold his/her breath is output. The length of time Ta of the breath-hold message a1 is of the order of 5 seconds, for example Since the subject holds his/her breath by the breath-hold message a1, the DAP scan SC0 can be conducted during the subject's breath-hold. After the DAP scan SC0 is completed, a voice message b1 for allowing the subject to restart breathing is output. The length of time Tb of the voice message b1 is of the order of 5 seconds, for example. The subject restarts breathing following the voice message b1. Thus, the DAP scan SC0 is conducted during a subject's breath-hold.

The DAP scan SC0 has two scans SC1 and SC2 for double imaging in an arterial phase. The scans SC1 and SC2 will now be described one by one.

The scan SC1 is a scan for acquiring data in an early arterial phase, and is started at a point in time after a period of time TW1 (sec) has elapsed from contrast medium administration. By conducting the scan SC1, data in the early arterial phase is acquired.

After the scan SC1 is completed, the next scan SC2 is conducted. The scan SC2 is a scan for acquiring data in a late arterial phase. The scan SC2 is started at a point in time after a period of time TW2 has elapsed from the start of the scan SC1. The period of time TW2 should be set to a time suitable for acquisition of data in the late arterial phase, and is set to 10 seconds, for example. Moreover, a delay time TD1 is placed between the scans SC1 and SC2. However, since the two scans SC1 and SC2 should be conducted during a subject's breath-hold in the DAP scan SC0, it is desirable that the delay time TD1 be ideally 0 second from a viewpoint of mitigation of stress experienced by the subject due to breath-holding. In case that TD1=0 second cannot be set because of some imaging conditions, performance of the MR apparatus, etc., the delay time TD1 is set to as short a time as possible (1 second, for example).

As described above, the two scans SC1 and SC2 are conducted during a subject's breath-hold in the DAP scan SC0. After the DAP scan SC0 is completed, a scan SC3 is conducted.

The scan SC3 is a scan for acquiring data in a portal phase. The scan SC3 is started at a point in time after a period of time TW3 has elapsed from the start of the scan SC1. The period of time TW3 should be set to a time suitable for acquisition of data in the portal phase, and is set to 60 seconds, for example. It should be noted that a delay time TD2 (sec) is placed between the DAP scan SC0 and scan SC3, and the period of time TW3 varies depending upon the value of the delay time TD2. Therefore, it is desired to set the delay time TD2 so that the period of time TW3 is set to a time suitable for acquisition of data in the portal phase. The delay time TD2 is 40 seconds, for example.

Similarly to the DAP scan SC0, the scan SC3 should be conducted during a subject's breath-hold. Therefore, before the scan SC3, a breath-hold message a2 for asking the subject to hold his/her breath is output. Since the subject holds his/her breath by the breath-hold message a2, the scan SC3 can be conducted during the subject's breath-hold. By conducting the scan SC3, data in the portal phase is acquired.

After the scan SC3 is completed, a restart-breathing message b2 for allowing the subject to restart breathing is output. The subject restarts breathing following the restart-breathing message b2. Thus, in acquiring data in the portal phase, the scan SC3 is conducted during a subject's breath-hold. After the scan SC3 is completed, a scan SC4 is conducted.

The scan SC4 is a scan for acquiring data in an equilibrium phase. The scan SC4 is started at a point in time after a period of time TW4 has elapsed from the start of the scan SC1. The period of time TW4 should be set to a time suitable for acquisition of data in the equilibrium phase, and is set to 2 minutes and 30 seconds, for example. It should be noted that a delay time TD3 (sec) is placed between the scans SC3 and SC4, and the period of time TW4 varies depending upon the value of the delay time TD3. Therefore, it is desirable to set the delay time TD3 so that the period of time TW4 is set to a time suitable for acquisition of data in the portal phase. The delay time TD3 is 1 minute and 20 seconds, for example.

Moreover, the scan SC4 should be conducted during a subject's breath-hold. Therefore, before the scan SC4, a breath-hold message a3 for asking the subject to hold his/her breath is output. Since the subject holds his/her breath by the breath-hold message a3, the scan SC4 can be conducted during the subject's breath-hold. By conducting the scan SC4, data in the equilibrium phase is acquired.

After the scan SC4 is completed, a restart-breathing message b3 for allowing the subject to restart breathing is output. The subject restarts breathing following the restart-breathing message b3. Thus, in acquiring data in the equilibrium phase, the scan SC4 is conducted during a subject's breath-hold. The main scan MS is thus conducted.

Now an operation of the MR apparatus in conducting the localizer scan LS and main scan MS in the present embodiment will be described.

Figure 4:
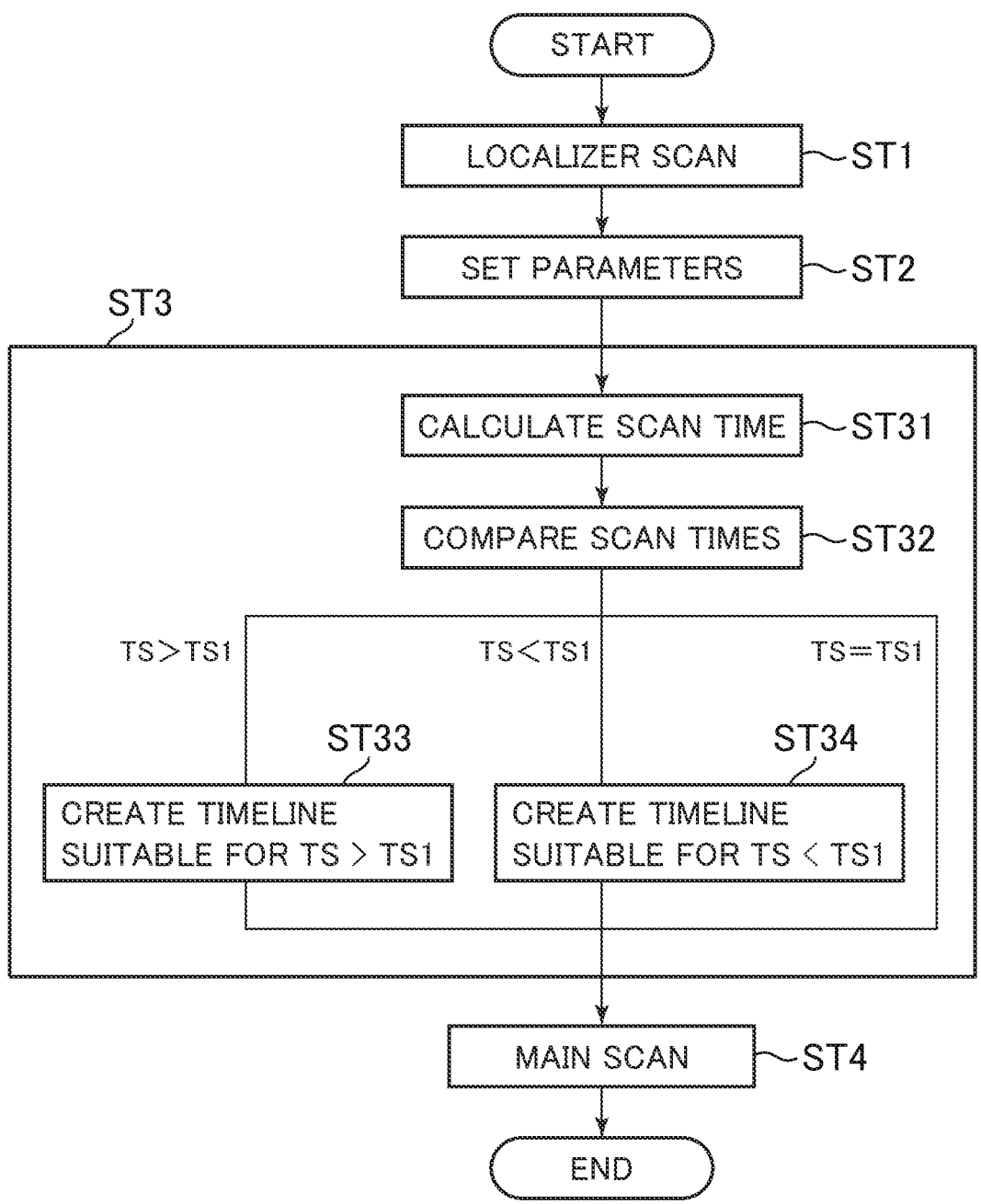
FIG. 4 shows a diagram showing flow of operation of the MR apparatus.

FIG. 4 is a diagram showing flow of operation of the MR apparatus. At Step ST1, a localizer scan is conducted. By conducting the localizer scan, an image for use in slice setting, etc. is obtained. After conducting the localizer scan, the flow goes to Step ST2.

At Step ST2, an operator sets parameter values (for example, the number of slices, resolution) in conducting a main scan MS while referring to the image obtained at Step ST1, etc. Once these parameter values have been set, the flow goes to Step ST3.

At Step ST3 is created a timeline defining a start point in time of each of the scans SC1-SC4 conducted in the main scan MS, etc. Now a method of creation of the timeline will be described.

In the present embodiment, a timelines serving as reference (referred to as reference timeline hereinbelow) in conducting the scans SC1-SC4 is saved in the memory 11.

Figure 5:
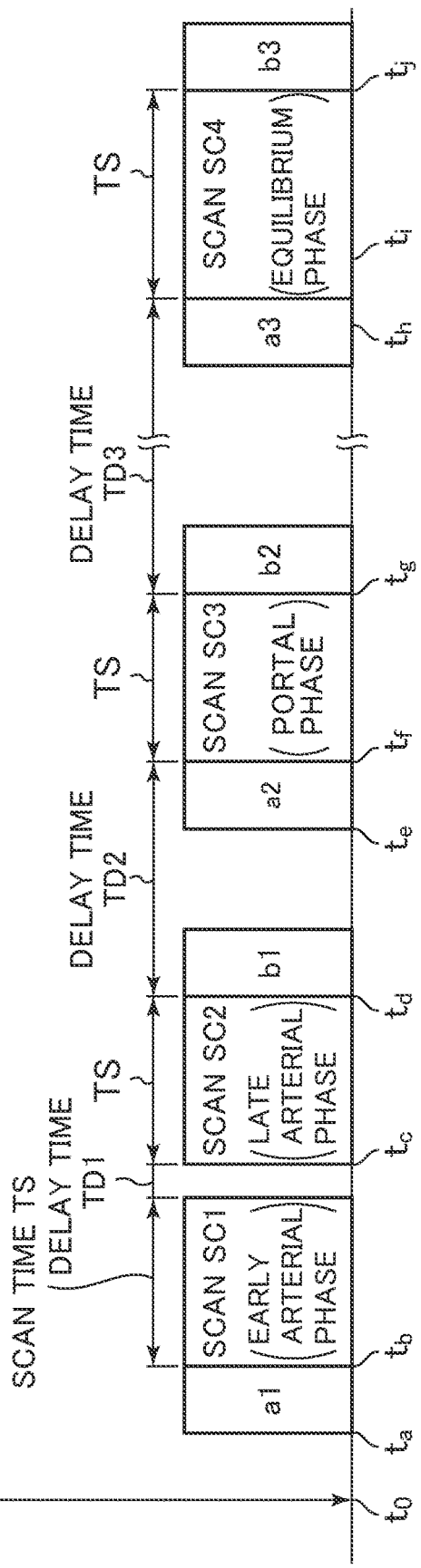
FIG. 5 shows a diagram showing a reference timeline TL0.

FIG. 5 is a diagram showing a reference timeline TL0. The reference timeline TL0 defines respective start points in time of the scans SC1-SC4 each having a scan time TS. It is assumed here that the scan time TS is defined such that TS=10 seconds. In FIG. 5, respective start points in time defined for the scans are designated by symbols "$t_b$," "$t_c$," "$t_f$," and "$t_i$."

Moreover, the reference timeline TL0 defines respective start points in time at which outputs of the breath-hold messages a1-a3 and restart-breathing messages b1-b3 are started. The respective start points in time defined for these messages are designated here by symbols "$t_a$," "$t_d$," "$t_e$," "$t_g$," "$t_h$," "$t_j$."

Further, the reference timeline TL0 defines delay times TD1, TD2, and TD3 each from the end of a scan to the start of a next scan. TD1, TD2, TD3 are such that TD1=1 second, TD2=30 seconds, and TD3=60 seconds, for example.

At Step ST3, an actual timeline in conducting the scans SC1-SC4 is determined referring to the reference timeline TL0 shown in FIG. 5. A procedure of determining the actual timeline will be described below.

At Step ST31, the software programs 101 (see FIG. 2) calculate a scan time of the scans SC1-SC4 based on the parameter values set by the operator at Step ST2. The calculated scan time is designated here as "TS1." After the scan time TS1 is calculated, the flow goes to Step ST32.

At Step ST32, the software programs 101 compare the scan time TS1 calculated at Step ST31 with the scan time TS in the reference timeline TL0.

In case that TS=TS1, the flow goes to Step ST4, in case that TS>TS1, the flow goes to Step ST33, and in case that TS<TS1, the flow goes to Step ST34. The following description of these steps will be made separately for the cases of TS=TS1, TS>TS1, and TS<TS1.

In the case in which TS=TS1, the flow goes to Step ST4, in which a scan is conducted following the reference timeline TL0 shown in FIG. 5.

First, at a point in time $t_0$, a contrast medium is administered. After the contrast medium is administered, an output of the breath-hold message a1 is started at the point in time $t_a$. The breath-hold message a1 is a voice message saying, for example, "Breathe in, breathe out, breathe in, breathe out, and hold your breath." The subject holds his/her breath in response to the breath-hold message a1. After the breath-hold message a1 is output, the scan SC1 is started at the point in time $t_b$. By conducting the scan SC1, data in the early arterial phase is acquired.

After the scan SC1 is completed, the scan SC2 is started at the point in time $t_c$ after the delay time TD1 has elapsed. The delay time TD1 is 1 second, for example. By conducting the scan SC2, data in the late arterial phase is acquired.

After the scan SC2 is completed, an output of the restart-breathing message b1 is started at the point in time $t_d$. The restart-breathing message hi is a voice message saying, for example, "Now you can freely breathe. Please relax." The subject restarts breathing in response to the message b1.

After the subject is allowed to restart breathing, an output of the breath-hold message a2 for asking the subject to hold his/her breath is started at the point in time $t_e$. The subject holds his/her breath in response to the breath-hold message a2. After the breath-hold message a2 is output, the scan SC3 is started at the point in time $t_f$. By conducting the scan SC3, data in the portal phase is acquired.

After the scan SC3 is completed, an output of the restart-breathing message b2 is started at the point in time $t_g$. The subject restarts breathing in response to the message b2.

After the subject is allowed to restart breathing, an output of the breath-hold message a3 for asking the subject to hold his/her breath is started at the point in time $t_h$. The subject holds his/her breath in response to the breath-hold message a3. After the breath-hold message a3 is output, the scan SC4 is started at the point in time $t_i$. By conducting the scan SC4, data in the equilibrium phase is acquired. After the scan SC4 is completed, the restart-breathing message b3 is output, and the flow is terminated.

In the case in which TS>TS1, healthy subjects may generally be able to hold their breath over a relatively long time. However, elderly people, for example, may have difficulty in breath-holding over a long time. Then, the operator sets parameter values so that the scan time is shortened for a subject supposed to have difficulty in breath-holding over a long time. Methods of shortening the scan time include a method of lowering the resolution of an FOV (field of view), for example. In case that parameter values causing a shorter scan time are set, the scan time TS1 calculated at Step ST31 is shorter than the scan time TS in the reference timeline TL0. For example, while the scan time TS is 10 seconds in the reference timeline TL0, the actually calculated scan time TS1 may be 8 seconds. In this case, since TS>TS1, the flow goes to Step ST33.

At Step ST33, a timeline suitable for the scan time TS1 is created based on the reference timeline TL0. A method of creation of the timeline will be described hereinbelow. In the following description, to clarify the effect of the present embodiment, a case in which the timeline is created by a method different from the method of the present embodiment will be first described, and then, a case in which the timeline is created by the method of the present embodiment will be described.

Figure 6:
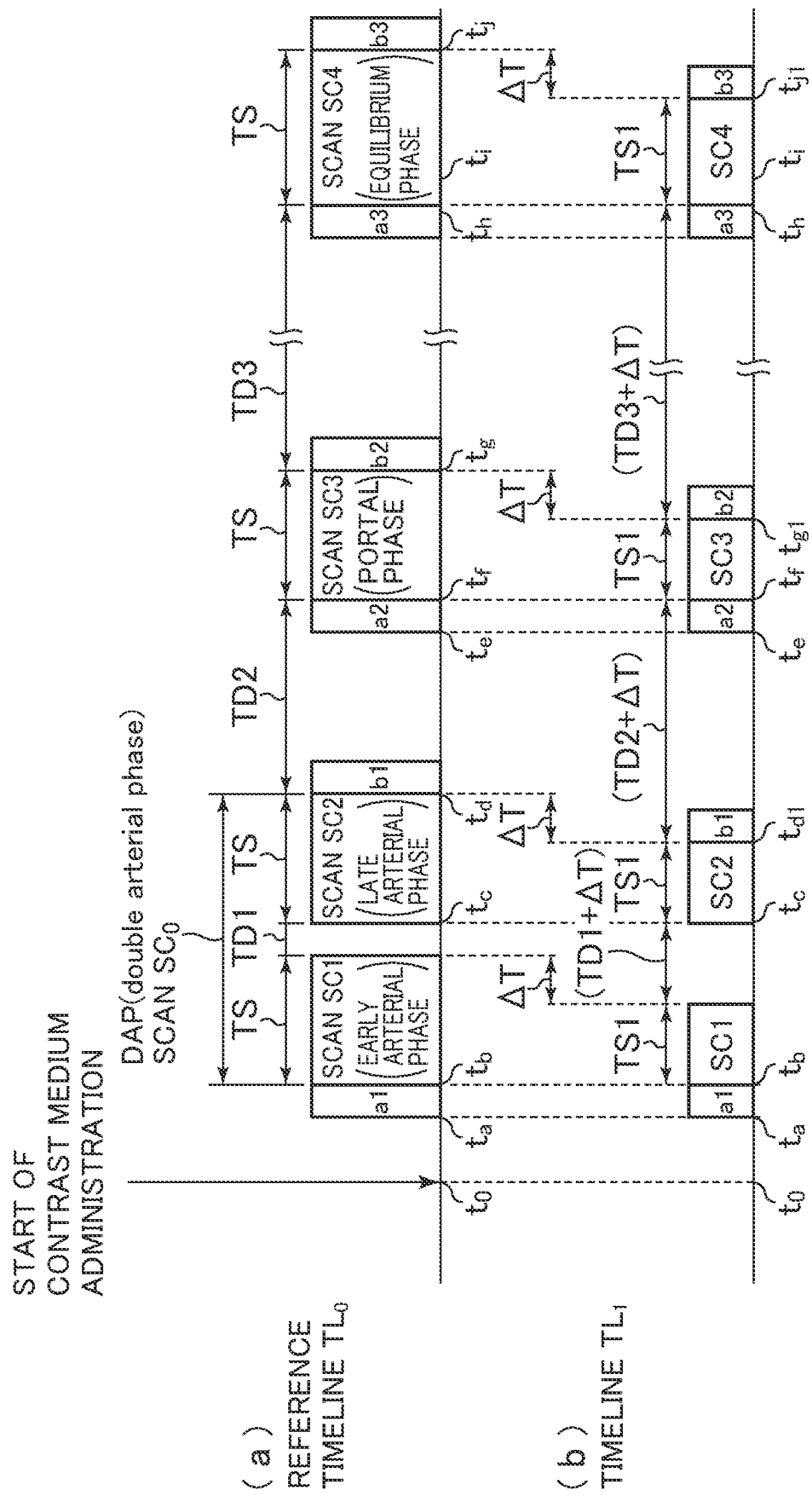
FIG. 6 shows a diagram explaining creation of a timeline by a method different from that of the present embodiment.

FIG. 6 is a diagram explaining a case in which a timeline is created by a method different from that in the present embodiment. FIG. 6(a) is a diagram showing the reference timeline TL0, and FIG. 6(b) is a diagram showing a timeline TL1 created by the method different from that in the present embodiment based on the reference timeline TL0.

The scan time of each scan in the timeline TL1 in FIG. 6(b) is TS1. Therefore, each of the scans in the timeline TL1 has a scan time shorter than that in the reference timeline TL0 by ΔT (=TS−TS1).

Moreover, the scans SC1-SC4 in the timeline TL1 keep the same start points in time as those in the reference timeline TL0. Therefore, the timeline TL1 has a delay time longer than that in the reference timeline TL0 by ΔT. In particular, in the timeline TL1, the delay time between the scans SC1 and SC2 is (TD1+ΔT), that between the scans SC2 and SC3 is (TD2+ΔT), and that between the scan SC3 and SC4 is (TD3+ΔT).

As the scan time becomes shorter, the start points in time of the restart-breathing messages b1, b2, and b3 are moved to respective points in time earlier by ΔT. The start point in time of the restart-breathing message b1 is moved from $t_d$ to $t_{d1}$, that of the restart-breathing message b2 is moved from $t_g$ to $t_{g1}$, and that of the restart-breathing message b3 is moved from $t_j$ to $t_{j1}$.

As described above, each of the scans in the timeline TL1 has a scan time shorter than that in the reference timeline TL0 by ΔT. Moreover, regarding the DAP scan SC0, it can be seen that the DAP scan SC0 in the timeline TL1 has a scan time shorter than that in the reference timeline TL0 by ΔT. Therefore, the period of time of a subject's breath-hold in conducting the DAP scan SC0 can be reduced by ΔT. For example, in case that the scan time TS in the reference timeline TL0 is TS=10 seconds and the delay time TD1 is TD1=1 second, the scan time of the DAP scan SC0 in the reference timeline TL0 is 21 seconds. In contrast, in case that the scan time TS1 in the timeline TL1 is TS1=7 seconds, the scan time of the DAP scan SC0 in the timeline TL1 is 18 seconds. Since the scan time is thus reduced by 3 seconds, the period of time of a subject's breath-hold in conducting the DAP scan SC0 can be reduced by 3 seconds.

However, subjects who have difficulty in breath-holding over a long time, such as elderly people, experience significant physical stress in breath-holding. Therefore, it is desired to further reduce the scan time of the DAP scan SC0. Thus, in the present embodiment, the software programs 101 create a timeline with which the scan time of the DAP scan SC0 can be further reduced. Now the method of creating such a timeline will be described (see FIG. 7).

Figure 7:
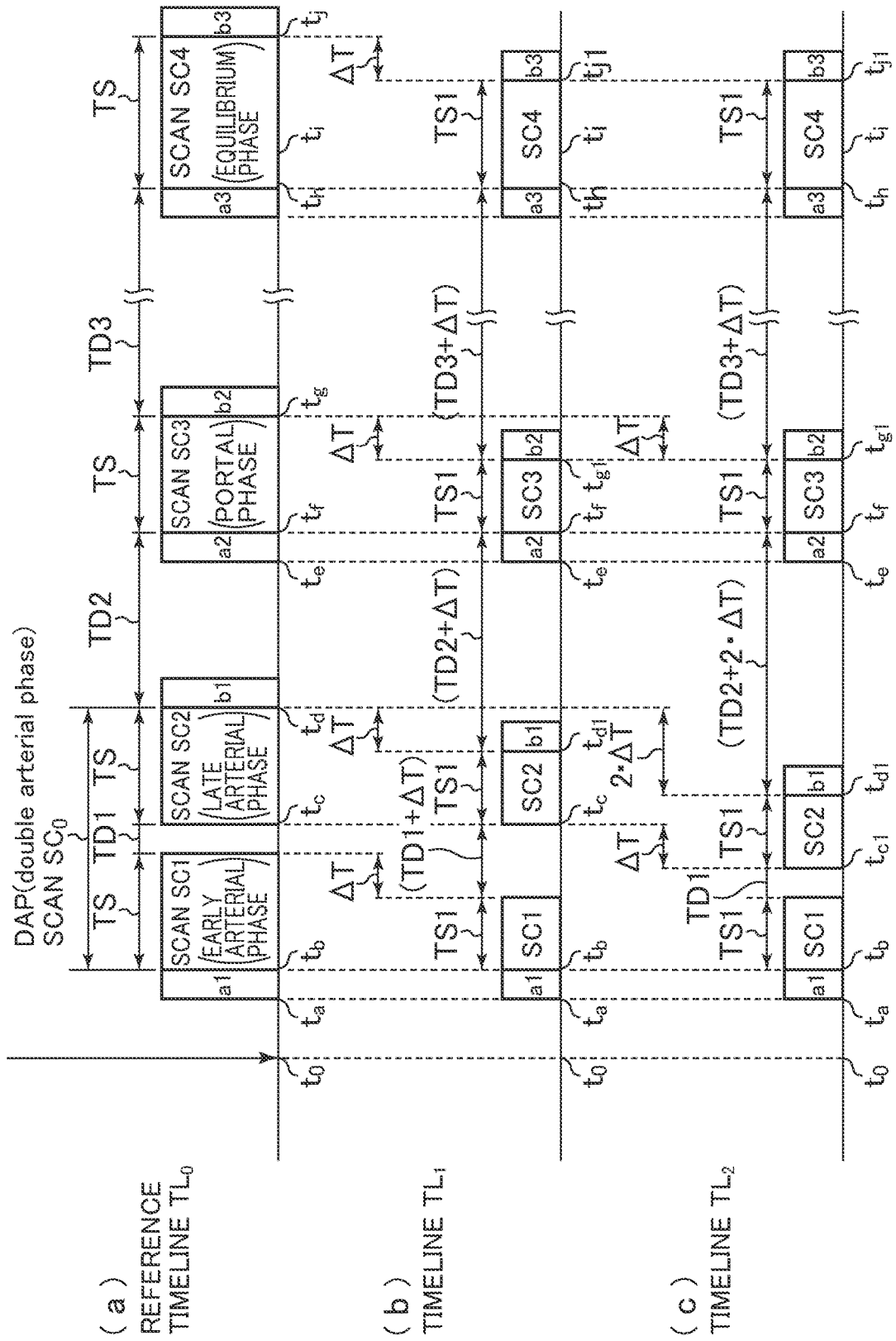
FIG. 7 shows a diagram explaining a method of creation of a timeline in the present embodiment.

FIG. 7 is a diagram explaining a method of creation of a timeline in the present embodiment. FIGS. 7(a) and (b) show again the same timelines as those in FIGS. 6(a) and (b), respectively. FIG. 7(c) shows a timeline TL2 obtained by the method of the present embodiment. The method of creation of the timeline TL2 will be described hereinbelow.

The software programs 101 keep the start point in time of the scan SC1 at $t_b$. The software programs 101 then calculate a start point in time $t_{c1}$ of the scan SC2. The start point in time $t_{c1}$ of the scan SC2 can be calculated by EQ. (1) as given below:

$$t_{c1} = t_b + TS1 + TD1 \qquad \text{EQ. (1)}$$

wherein:
    $t_b$: the start point in time of the scan SC1,
    TS1: the scan time of the scan SC1, and
    TD1: the delay time between the scans SC1 and SC2 in the reference timeline TL0.

It can be seen from EQ. (1) that the start point in time $t_{c1}$ of the scan SC2 in the timeline TL2 is set to a point in time earlier than the start point in time $t_c$ of the scan SC2 in the reference timeline TL0 by ΔT. Moreover, since the scan time of the scan SC2 is TS1, the scan SC2 is completed at a point in time $t_{d1}$. Since the timeline TL2 thus has a scan time of the DAP scan SC0 shorter than that in the reference timeline TL0 by 2·ΔT, it can be seen that the period of time of a subject's breath-hold can be reduced by 2·ΔT.

Therefore, the timeline TL2 (see FIG. 7(c)) has a period of time of a subject's breath-hold in conducting the DAP scan SC0 further reduced by ΔT as compared with the timeline TL1 (see FIG. 7(b)), so that stress experienced by the subject in breath-holding can be mitigated.

Next, the software programs 101 calculate a start point in time $t_f$ of the scan SC3. The start point in time $t_f$ of the scan SC3 can be calculated by EQ. (2) as given below:

$$t_f = t_{c1} + TS1 + 2 \cdot \Delta T + TD2 \quad \text{EQ. (2)}$$

wherein:
$t_{c1}$: the start point in time of the scan SC2,
TS1: the scan time of the scan SC2,
ΔT: the difference in time between the scan times TS and TS1, and
TD2: the delay time between the scans SC2 and SC3 in the reference timeline TL0.

It can be seen from EQ. (2) that the start point in time $t_f$ of the scan SC3 in the timeline TL2 is set to the same point in time as that in the reference timeline TL0. Therefore, data in the portal phase may be acquired at the most suitable time. It should be noted that the scan SC3 in the timeline TL2 is completed earlier than that in the reference timeline TL0 by ΔT.

Next, the software programs 101 calculate a start point in time $t_i$ of the scan SC4. The start point in time $t_i$ of the scan SC4 can be calculated by EQ. (3) as given below:

$$t_i = t_f + TS1 + \Delta T + TD3 \quad \text{EQ. (3)}$$

wherein:
$t_f$: the start point in time of the scan SC3,
TS1: the scan time of the scan SC3,
ΔT: the difference in time between the scan times TS and TS1, and
TD3: the delay time between the scans SC3 and SC4 in the reference timeline TL0.

It can be seen from EQ. (3) that the start point in time $t_{c1}$ of the scan SC4 in the timeline TL2 is set to the same point in time as that in the reference timeline TL0. Therefore, data in the equilibrium phase may be acquired at the most suitable time. It should be noted that the scan SC4 in the timeline TL2 is completed earlier than that in the reference timeline TL0 by ΔT.

Moreover, in the timeline TL2, the time of the end of each scan is earlier as compared with the reference timeline TL0. The software programs 101 then modify the start points in time of the restart-breathing messages b1, b2, and b3 as well in synchronization with the times at which the respective scans are completed. The start point in time of the restart-breathing message b1 is modified to a point in time $t_{d1}$ that is earlier than $t_d$ by 2·ΔT. The start point in time of the restart-breathing message b2 is modified to a point in time $t_{g1}$ that is earlier than $t_g$ by ΔT, and that of the restart-breathing message b3 is modified to a point in time $t_{j1}$ that is earlier than $t_j$ by ΔT. Therefore, although the time of the end of each scan is modified, the restart-breathing messages can be output immediately after the end of the scans.

Figure 8:
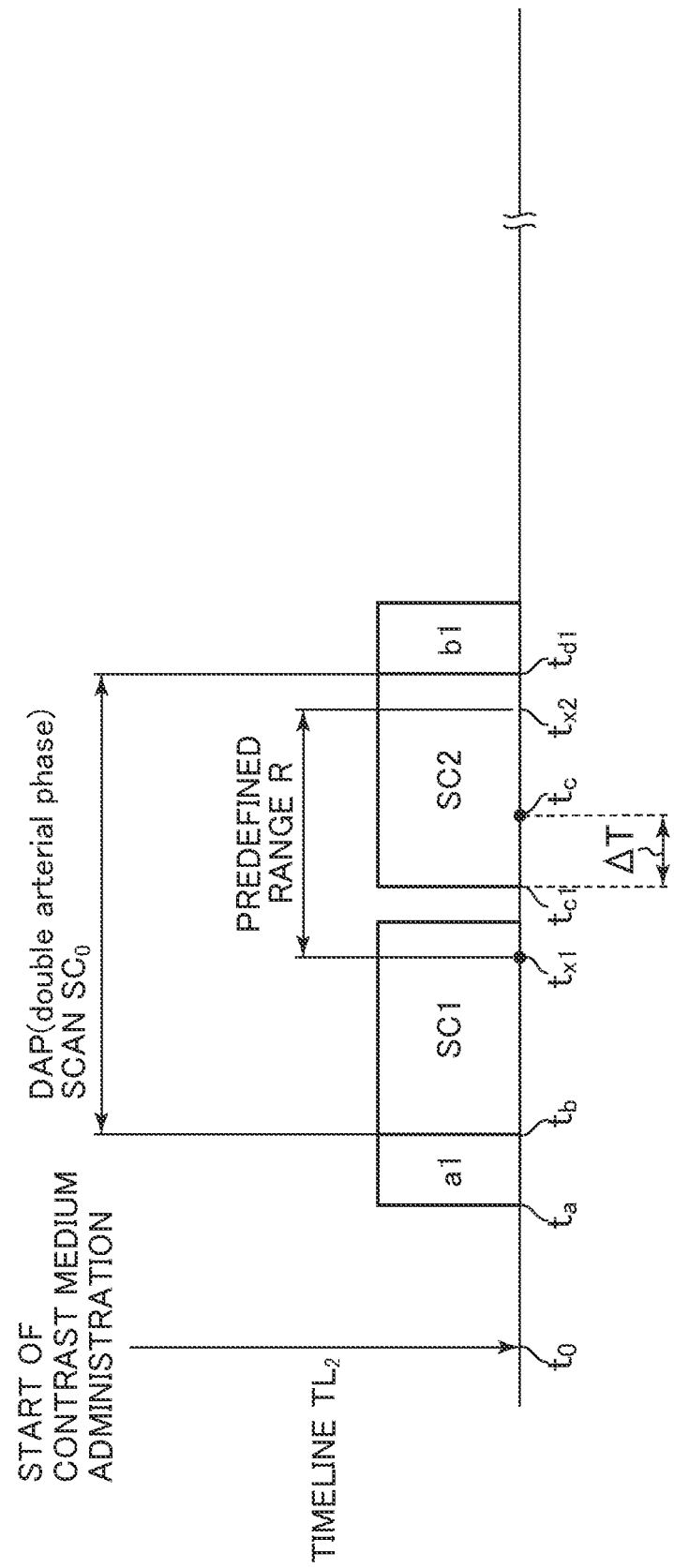
FIG. 8 shows a diagram schematically showing a case in which $t_{c1}$ falls within a predefined range R.

It should be noted that the time of the start of the scan SC2 is modified from $t_c$ to $t_{c1}$ in the timeline TL2. However, the shift of $t_{c1}$ from $t_c$ causes no problem insofar as $t_{c1}$ falls within a predefined range. FIG. 8 schematically shows a case in which $t_{c1}$ falls within a predefined range R. In FIG. 8, a range from a point in time $t_{x1}$ to a point in time $t_{x2}$ is defined as the predefined range R. The point in time $t_{x1}$ may be set to, for example, a point in time after 8 seconds have elapsed from the start point in time $t_b$ of the scan SC1, while the point in time $t_{x2}$ may be set to, for example, a point in time after 12 seconds have elapsed from the start point in time $t_b$ of the scan SC1. Since data in the late arterial phase that is useful in diagnosis can be acquired insofar as $t_{c1}$ in the timeline TL2 falls within the range from $t_{x1}$ to $t_{x2}$, the shift of $t_{c1}$ relative to $t_c$ by ΔT causes no problem. However, $t_{c1}$ may sometimes lie outside of the predefined range R depending upon the value of ΔT. In this case, data in the late arterial phase that is useful in diagnosis cannot be acquired. Therefore, it is desirable that the software programs 101 decide whether $t_{c1}$ falls within the predefined range R. In case that $t_{c1}$ is decided not to fall within the predefined range R, the operator may be given a warning stating that modification of the start point in time $t_{c1}$ is required. By this warning, the operator can find that the start point in time $t_{c1}$ of the scan SC2 is unsuitable, and accordingly, he/she can modify the start point in time $t_{c1}$ before conducting the main scan MS. After the timeline TL2 is created, the flow goes to Step ST4.

At Step ST4, the main scan is conducted following the timeline TL2 shown in FIG. 7(c). First, at the point in time $t_0$, a contrast medium is administered. After the contrast medium is administered, an output of the breath-hold message a1 is started at the point in time $t_a$. The subject holds his/her breath in response to the breath-hold message a1. After the breath-hold message a1 is output, the scan SC1 is started at the point in time $t_b$. By conducting the scan SC1, data in the early arterial phase is acquired.

After the scan SC1 is completed, the scan SC2 is started at the point in time $t_{c1}$ after the delay time TD1 has elapsed. The delay time TD1 is 1 second, for example. By conducting the scan SC2, data in the late arterial phase is acquired.

After the scan SC2 is completed, an output of the restart-breathing message b1 is started at the point in time $t_{d1}$. The subject restarts breathing in response to the message b1.

After the subject is allowed to restart breathing, an output of the breath-hold message a2 for asking the subject to hold his/her breath is started at the point in time $t_e$. The subject holds his/her breath in response to the breath-hold message a2. After the breath-hold message a2 is output, the scan SC3 is started at the point in time $t_f$. By conducting the scan SC3, data in the portal phase is acquired.

After the scan SC3 is completed, an output of the restart-breathing message b2 is started at the point in time $t_{g1}$. The subject restarts breathing in response to the message b2.

After the subject is allowed to restart breathing, an output of the breath-hold message a3 for asking the subject to hold his/her breath is started at the point in time $t_h$. The subject holds his/her breath in response to the breath-hold message a3. After the breath-hold message a3 is output, the scan SC4 is started at the point in time $t_i$. By conducting the scan SC4, data in the equilibrium phase is acquired. After the scan SC4 is completed, the restart-breathing message b3 is output, and the flow is terminated.

Since the timeline TL2 can further reduce the scan time of the DAP scan SC0 by ΔT as compared with the timeline TL1, stress experienced by the subject during a breath-hold can be further mitigated.

Moreover, since the start points in time of the scans SC3 and SC4 are kept at the same points in time ($t_f$ and $t_i$) as those in the reference timeline TL0 although the scan time of each scan is shortened, data acquisition can be achieved under conditions suitable for the portal phase and equilibrium phase.

In the case in which TS<TS1, an image having as high a resolution as possible is required in making image diagnosis, the operator sets parameter values such that the image resolution is enhanced. When parameter values are set such that the image resolution is enhanced, however, the amount of data to be acquired is increased, so that the scan time TS1 calculated at Step ST31 may sometimes be longer than the scan time TS of the reference timeline TL0. For example, while the scan time TS of the reference timeline TL0 is 10 seconds, the actually calculated scan time TS1 may be 12 seconds. In this case, TS<TS1, and accordingly, the flow goes to Step ST34.

At Step ST34, a timeline suitable for TS<TS1 is created based on the reference timeline TL0.

Figure 9:
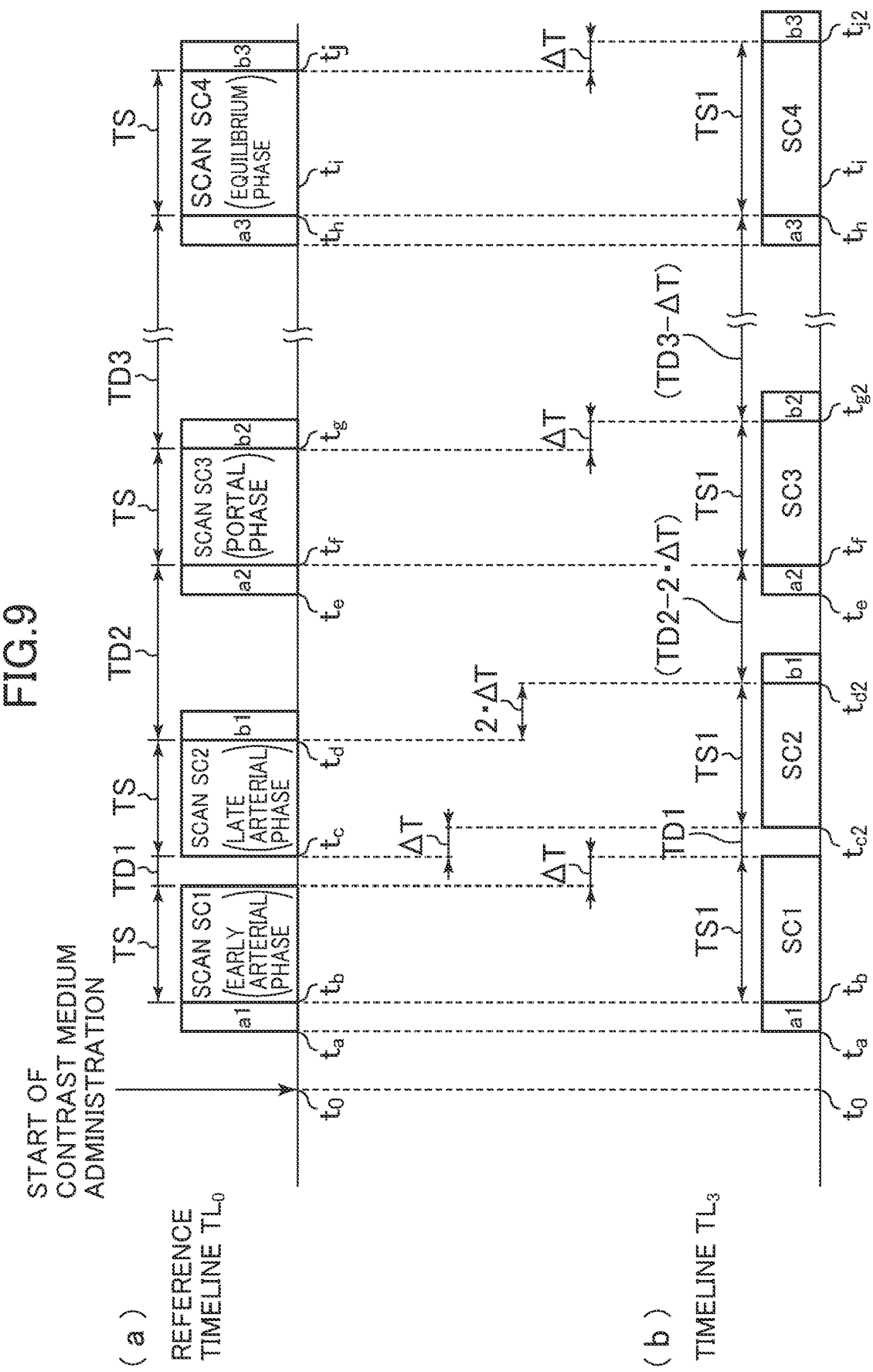
FIG. 9 shows a diagram explaining the method of creation of a timeline in case that TS<TS1.

FIG. 9 is a diagram explaining a method of creation of a timeline in case that TS<TS1. FIG. 9(a) shows the reference timeline TL0, and FIG. 9(b) shows a timeline TL3 obtained by the method of the present embodiment in case that TS<TS1.

In FIG. 9, a difference between the scan times TS1 and TS is designated as ΔT. The software programs 101 keep the start point in time of the scan SC1 at $t_b$. The software programs 101 then calculate a start point in time $t_{c2}$ of the scan SC2. The start point in time $t_{c2}$ of the scan SC2 can be calculated using EQ. (4) as given below:

$$t_{c2} = t_b + TS1 + TD1 \qquad \text{EQ. (4)}$$

wherein:
$t_b$: the start point in time of the scan SC1,
TS1: the scan time of the scan SC1, and
TD1: the delay time between the scans SC1 and SC2 in the reference timeline TL0.

It can be seen from EQ. (4) that the start point in time $t_{c2}$ of the scan SC2 in the timeline TL3 is set to a point in time later than that in the reference timeline TL0 by ΔT. Moreover, since the scan time of the scan SC2 is TS1, the scan SC2 is completed at a point in time $t_{d2}$. Therefore, it can be seen that the timeline TL3 has a scan time of the DAP scan SC0 longer than that in the reference timeline TL0 by 2·ΔT.

Next, the software programs 101 calculate a start point in time $t_f$ of the scan SC3. The start point in time $t_f$ of the scan SC3 can be calculated by EQ. (5) as given below:

$$t_f = t_{c2} + TS1 + 2 \cdot \Delta T + TD2 \qquad \text{EQ. (5)}$$

wherein:
$t_{c2}$: the start point in time of the scan SC2,
TS1: the scan time of the scan SC2,
ΔT: the difference in time between the scan times TS and TS1, and
TD2: the delay time between the scans SC2 and SC3 in the reference timeline TL0.

It can be seen from EQ. (5) that the start point in time $t_f$ of the scan SC3 in the timeline TL3 is set to the same point in time as that in the reference timeline TL0. Therefore, data in the portal phase can be acquired at the most suitable time. It should be noted that the scan SC3 in the timeline TL3 is completed later than that in the reference timeline TL0 by ΔT.

Next, the software programs 101 calculate a start point in time $t_i$ of the scan SC4. The start point in time $t_i$ of the scan SC4 can be calculated by EQ. (6) as given below:

$$t_i = t_f = TS1 - \Delta T + TD3 \qquad \text{EQ. (6)}$$

wherein:
$t_f$: the start point in time of the scan SC3,
TS1: the scan time of the scan SC3,
ΔT: the difference in time between the scan times TS and TS1, and
TD3: the delay time between the scans SC3 and SC4 in the reference timeline TL0.

It can be seen from EQ. (6) that the start point in time $t_i$ of the scan SC4 in the timeline TL3 is set to the same point in time as that in the reference timeline TL0. Therefore, data in the equilibrium phase can be acquired at the most suitable time. It should be noted that the scan SC4 in the timeline TL3 is completed later than that in the reference timeline TL0 by ΔT.

Moreover, in the timeline TL3, the time of the end of each scan is later as compared with the reference timeline TL0. The software programs 101 then modify the start points in time of the restart-breathing messages b1, b2, and b3 as well in synchronization with the times at which the respective scans are completed. The start point in time of the restart-breathing message b1 is modified to a point in time $t_{d2}$ that is later than $t_d$ by 2·ΔT. The start point in time of the restart-breathing message b2 is modified to a point in time $t_{g2}$ that is later than $t_g$ by ΔT, and that of the restart-breathing message b3 is modified to a point in time $t_{j2}$ that is later than $t_j$ by ΔT. Therefore, although the time of the end of each scan is modified, the restart-breathing messages can be output immediately after the end of the scans.

It should be noted that the time of the start of the scan SC2 is modified to $t_{c2}$ in the timeline TL3. However, the shift of $t_{c2}$ from $t_c$ causes no problem insofar as $t_{c2}$ falls within the predefined range R shown in FIG. 8. In case that $t_{c2}$ lies outside of the predefined range R, the operator may be given a warning stating that modification of the start point in time $t_{c2}$ is required. By this warning, the operator can find that the start point in time $t_{c2}$ is unsuitable, and accordingly, he/she can modify the start point in time $t_{c2}$. After the timeline TL3 is adjusted, the flow goes to Step ST4.

At Step ST4, the scan is conducted following the timeline TL3 shown in FIG. 9(b). First, at the point in time $t_0$, a contrast medium is administered. After the contrast medium is administered, an output of the breath-hold message a1 is started at the point in time $t_a$. The subject holds his/her breath in response to the breath-hold message a1. After the breath-hold message a1 is output, the scan SC1 is started at the point in time $t_b$. By conducting the scan SC1, data in the early arterial phase is acquired.

After the scan SC1 is completed, the scan SC2 is started at the point in time $t_{c2}$ after the delay time TD1 has elapsed. The delay time TD1 is 1 second, for example. By conducting the scan SC2, data in the late arterial phase is acquired.

After the scan SC2 is completed, an output of the restart-breathing message b1 is started at the point in time $t_{d2}$. The subject restarts breathing in response to the message b1.

After the subject is allowed to restart breathing, an output of the breath-hold message a2 for asking the subject to hold his/her breath is started at the point in time $t_e$. The subject holds his/her breath in response to the breath-hold message a2. After the breath-hold message a2 is output, the scan SC3 is started at the point in time $t_f$. By conducting the scan SC3, data in the portal phase is acquired.

After the scan SC3 is completed, an output of the restart-breathing message b2 is started at the point in time $t_{g2}$. The subject restarts breathing in response to the message b2.

After the subject is allowed to restart breathing, an output of the breath-hold message a3 for asking the subject to hold his/her breath is started at the point in time $t_h$. The subject holds his/her breath in response to the breath-hold message a3. After the breath-hold message a3 is output, the scan SC4 is started at the point in time $t_i$. By conducting the scan SC4, data in the equilibrium phase is acquired.

After the scan SC4 is completed, the restart-breathing message b3 is output, and the flow is terminated.

While in the timeline TL3, the scan time of each scan is longer than that in the reference timeline TL0 by $\Delta T$, the times of the start of the scans SC3 and SC4 are kept at the same points in time ($t_f$ and $t_i$) as those in the reference timeline TL0. Therefore, although the scan time is lengthened, data acquisition can be achieved under conditions suitable for the portal phase and equilibrium phase.

Figure 10:
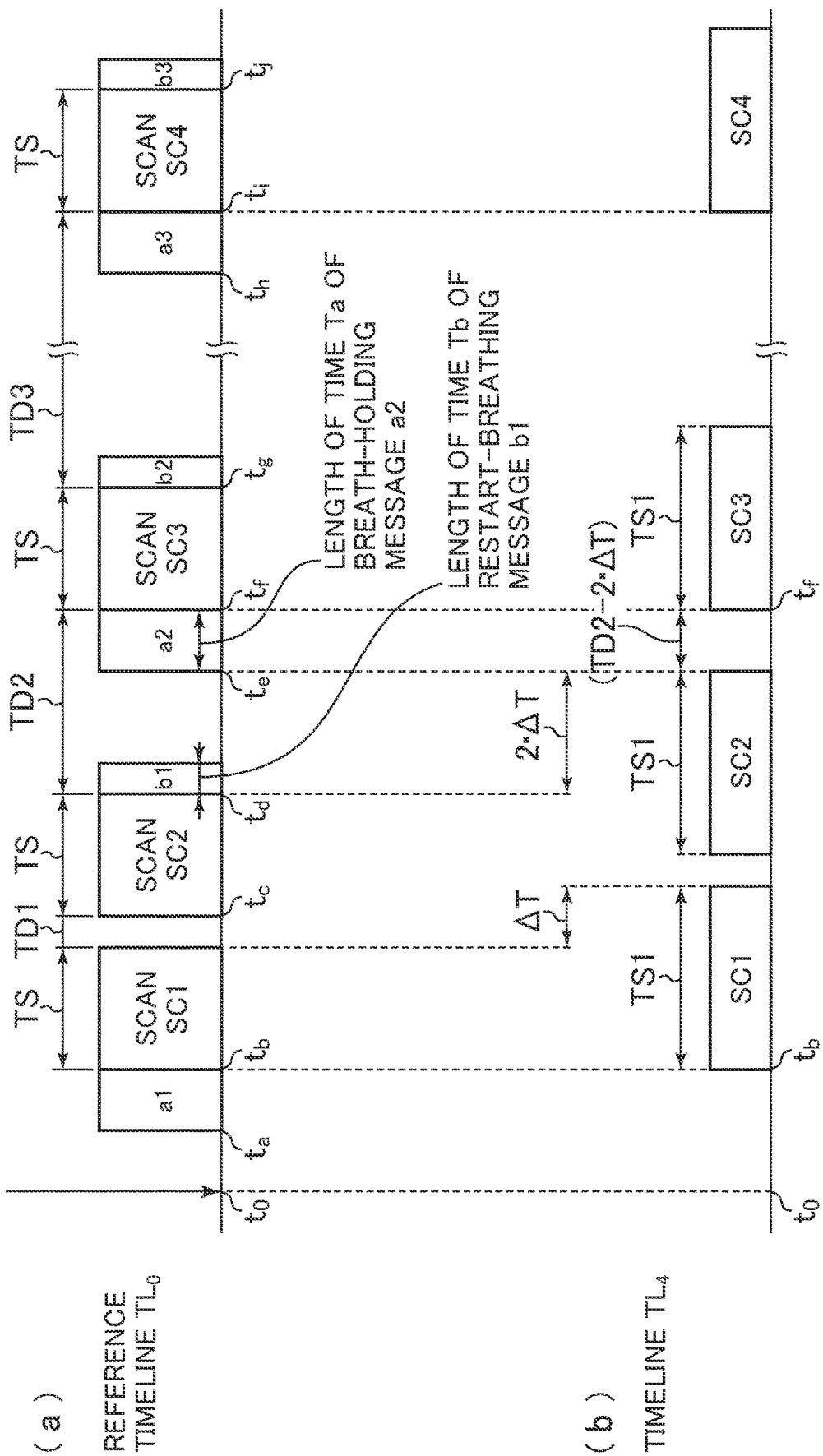
FIG. 10 shows a diagram showing a timeline TL4 in which a delay time (TD2−2·ΔT) is too small.

It should be noted that as the difference $\Delta T$ in scan time becomes larger, the delay time (TD2−2·$\Delta T$) between the scans SC2 and SC3 is decreased. Therefore, the delay time (TD2−2·$\Delta T$) may sometimes be too small depending upon the value of $\Delta T$. A timeline TL4 having too small a delay time (TD2−2·$\Delta T$) is shown in FIG. 10. It is necessary to output both the restart-breathing message b1 and breath-hold message a2 between the scans SC2 and SC3. Therefore, representing the length of time of the restart-breathing message b1 as "Tb" and that of the breath-hold message a2 as "Ta," the delay time (TD2−2·$\Delta T$) is required to satisfy the following relationship with respect to Tb and Ta:

$$TD2-2\cdot\Delta T \geq Tb+Ta \qquad \text{EQ. 7}$$

Figure 11:
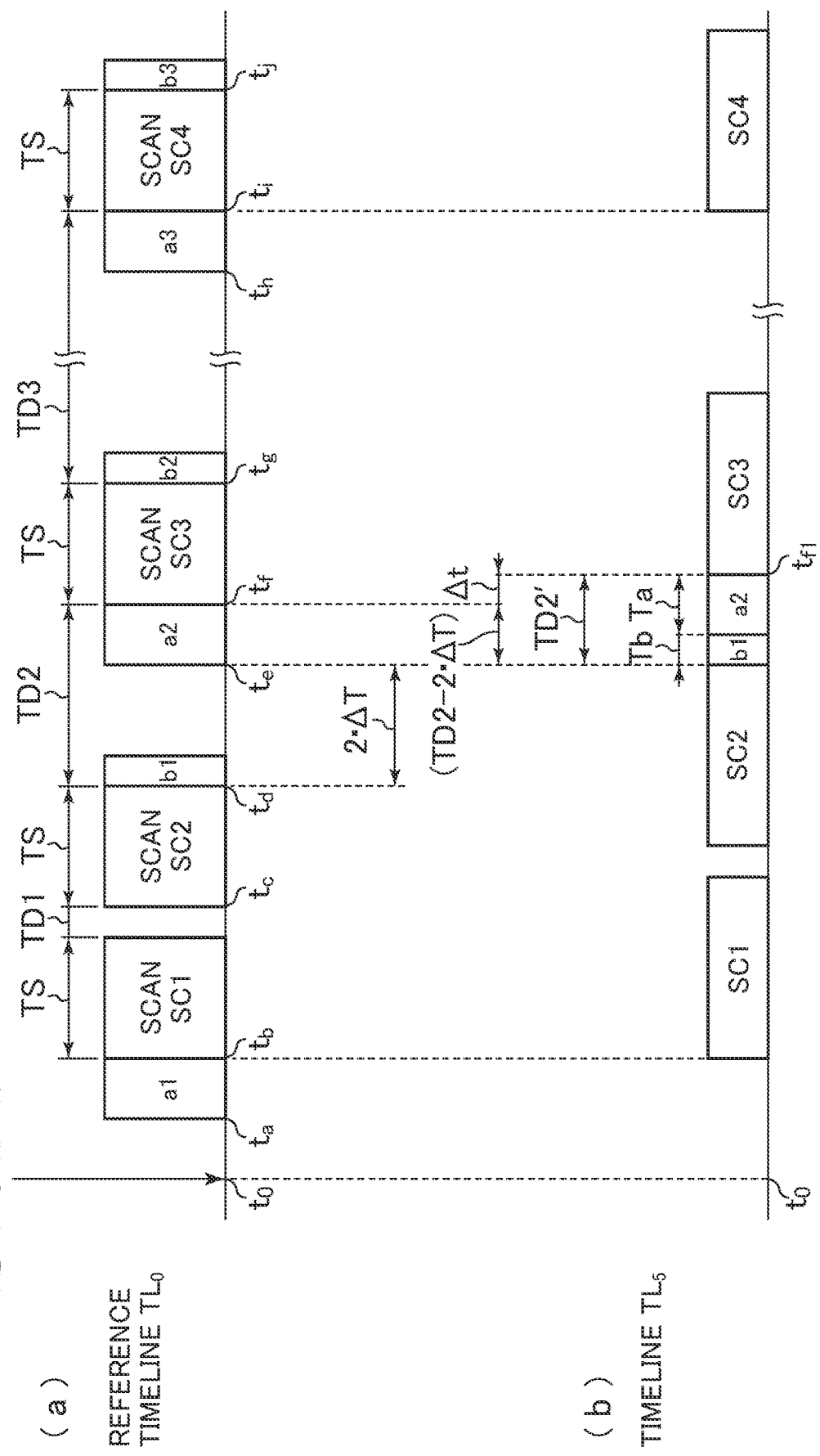
FIG. 11 shows a diagram showing a timeline TL5 in which a start point in time of a scan SC3 is modified to a point in time in delayed from $t_f$ by Δt.

In FIG. 10, however, the delay time (TD2−2·$\Delta T$) is approximately the same as the length of time Ta of the breath-hold message a2, so that both the restart-breathing message b1 and breath-hold message a2 cannot be output during the delay time (TD2−2·$\Delta T$). Then, in case that both the messages b1 and a2 cannot be output during the delay time (TD2−2·$\Delta T$), it is desirable to modify the start point in time of the scan SC3 to a point in time $t_{f1}$ that is later than $t_f$. FIG. 11 shows a timeline TL5 in which the start point in time of the scan SC3 is modified to the point in time $t_{f1}$ that is later than $t_f$ by $\Delta t$. In this case, the delay time between the scans SC2 and SC3 is "TD2'." TD2' is represented by the following equation:

$$TD2'=TD2-2\cdot\Delta T+\Delta t \qquad \text{EQ. 8}$$

Thus, by modifying the start point in time of the scan SC3 to the point in time $t_{f1}$ that is later than $t_f$, the delay time TD2' becomes longer than (TD2−2·$\Delta T$) by $\Delta t$. Therefore, by adjusting the length of $\Delta t$, both the messages b1 and a2 can be output during the delay time TD2'.

Since the length of time of the restart-breathing message b1 is Tb and that of the breath-hold message a2 is Ta, the delay time TD2' may be made to satisfy the equation below to output both the messages during the delay time TD2':

$$TD2' \geq Tb+Ta \qquad \text{EQ. 9}$$

Figure 12:
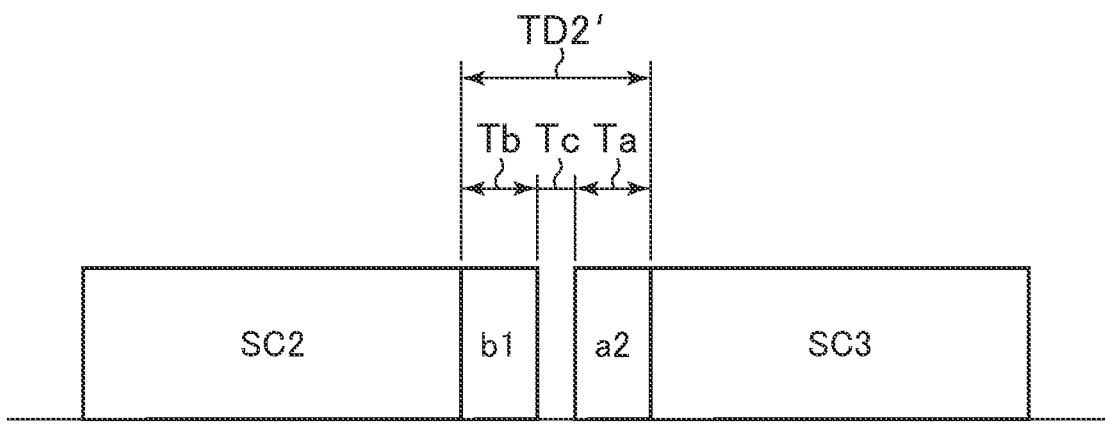
FIG. 12 shows a diagram showing a lower limit value of TD2' when a specific interval Tc is placed between a restart-breathing message a1 and a breath-hold message b2.

It can be seen from EQ. (9) that both the messages can be output during the delay time TD2' when TD2' has a value no less than (Tb+Ta). Therefore, the lower limit value of TD2' is (Ta+Tb). In case that TD2'=Ta+Tb, however, the subject restarts breathing following the restart-breathing message b1 and immediately after that the breath-hold message a2 is given, so that the subject must hold his/her breath immediately after he/she has restarted breathing, which results in higher physical stress experienced by the subject. Then, it is desirable to define a lower limit value of TD2' so that a specific interval can be placed between the restart-breathing message a1 and breath-hold message b2. FIG. 12 shows the lower limit value of TD2' in case that a specific interval Tc is placed between the restart-breathing message a1 and breath-hold message b2. By thus placing the interval Tc, the subject's physical stress can be mitigated.

Figure 13:
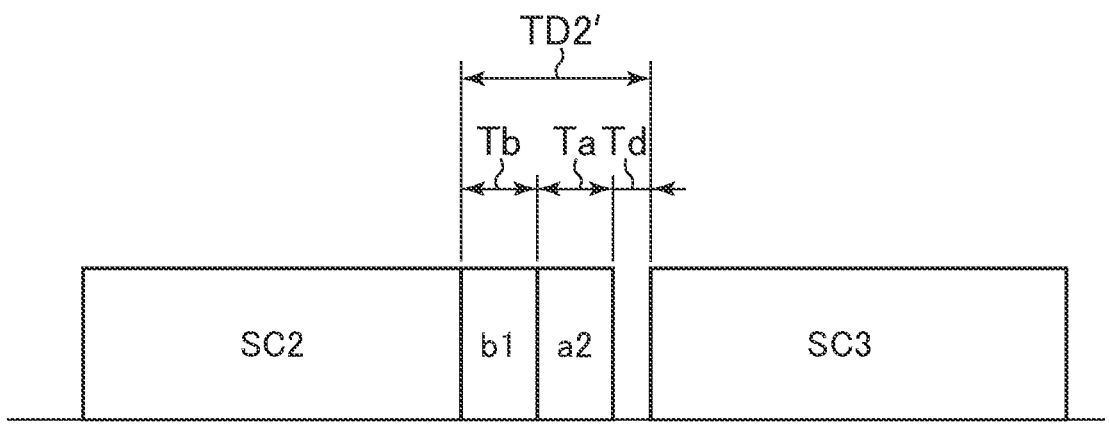
FIG. 13 shows a diagram schematically showing a lower limit value of the delay time TD2' when a specific interval Td is placed between a breath-hold message a2 and a scan SC3.

Moreover, when the subject holds his/her breath in response to the breath-hold message a2, it may take a specific time for the subject to react the breath-hold message a2 and hold his/her breath. Therefore, to start the scan SC3 after the subject has surely held his/her breath, a lower limit value of TD2' may be defined so that a specific interval is placed between the breath-hold message a2 and scan SC3 on account of a time lag in the subject's breath-hold. FIG. 13 schematically shows a lower limit value of the delay time TD2' in case that a specific interval Td is placed between the breath-hold message a2 and scan SC3. By placing the interval Td, the scan SC3 can be prevented from starting before the subject completes breath-holding. Further, both of the intervals Tc and Td may be placed in the delay time TD2'.

Figure 14:
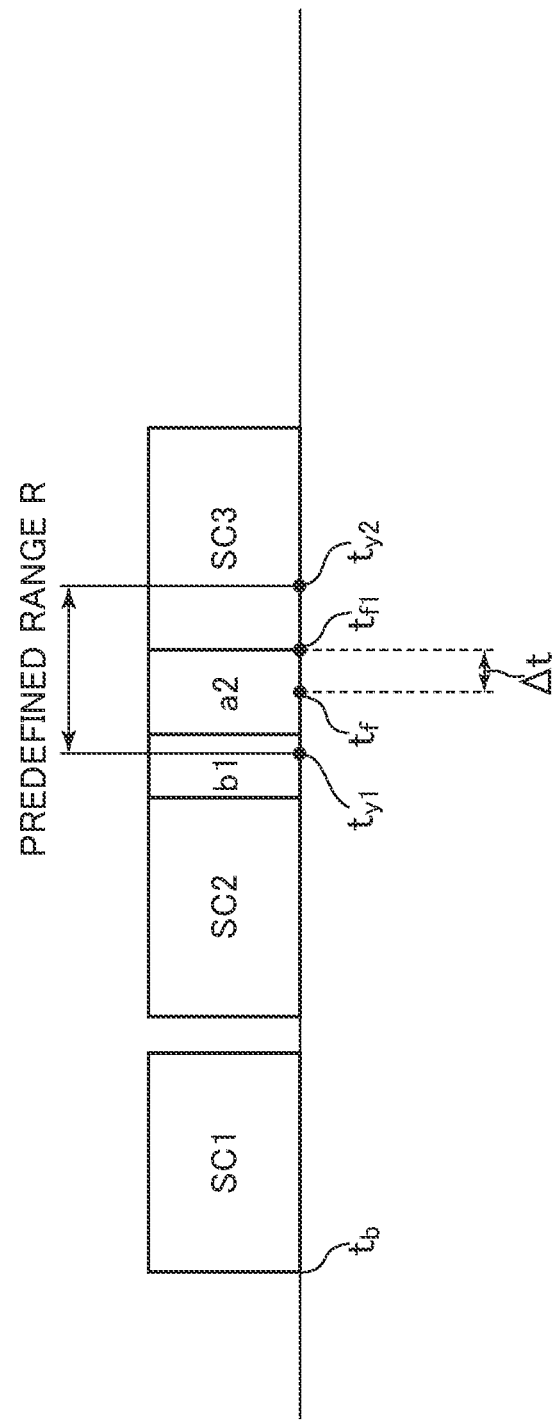
FIG. 14 shows a diagram schematically showing a case in which tn falls within a predefined range R.

In the timeline TL5 (see FIG. 11), the time of the start of the scan SC3 is modified from $t_f$ to $t_{f1}$. However, the shift of $t_{f1}$ from $t_f$ causes no problem insofar as $t_{f1}$ falls within a predefined range. FIG. 14 schematically shows a case in which $t_{f1}$ falls within a predefined range R. In FIG. 14, a range from a point in time $t_{y1}$ to a point in time $t_{y2}$ is defined as the predefined range R. The point in time $t_{y1}$ may be set to, for example, a point in time after 55 seconds have elapsed from the start point in time $t_b$ of the scan SC1, while the point in time $t_{y2}$ may be set to, for example, a point in time after 65 seconds have elapsed from the start point in time $t_b$ of the scan SC1. Since data in the portal phase that is useful in diagnosis can be acquired insofar as the start point in time $t_f$ of the scan SC3$_1$ falls within a range from $t_{y1}$ to $t_{y2}$, the shift of $t_{f1}$ with respect to $t_f$ by $\Delta t$ causes no problem. However, $t_{f1}$ may sometimes lie outside of the predefined range R depending upon the value of $\Delta t$. In this case, data in the portal phase that is useful in diagnosis cannot be acquired. Therefore, it is desirable that the software programs 101 decide whether $t_{f1}$ falls within the predefined range R. In case that $t_{f1}$ is decided not to fall within the predefined range R, the operator may be given a warning stating that modification of the start point in time $t_{f1}$ is required. By this warning, the operator can find that the start point in time $t_{f1}$ of the scan SC3 is unsuitable, and accordingly, he/she can modify the start point in time $t_{f1}$ before conducting the main scan MS.

Figure 15:
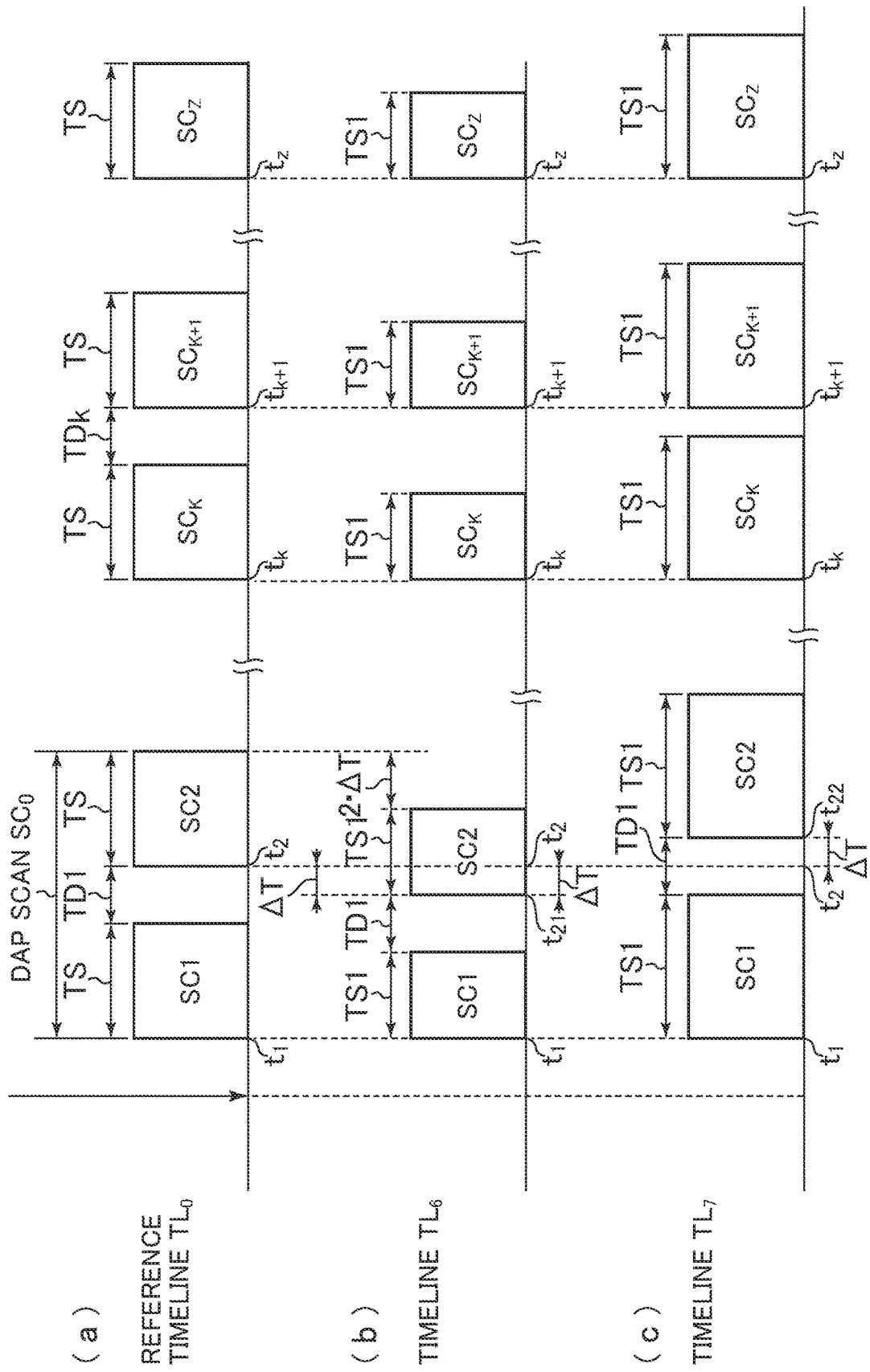
FIG. 15 shows a diagram schematically showing a timeline for scans SC1-SCz conducted for acquiring data in z (≥3) temporal phases.

It should be noted that the description of the present embodiment addresses a case in which scans in four temporal phases are conducted. However, the present invention is not limited to four temporal phases, and may be applied to scans for acquiring data in three or more temporal phases. FIG. 15 schematically shows a timeline in which scans SC1-SCz for acquiring data in z (≥3) temporal phases are conducted. FIG. 15(a) shows a reference timeline TL0 serving as reference in conducting the scans SC1-SCz, (b) shows a timeline TL6 in which the scan time TS1 is shorter than the scan time TS, and (c) shows a timeline TL7 in which the scan time TS1 is longer than the scan time TS. In FIG. 15, the breath-hold messages and restart-breathing messages are omitted for convenience of explanation.

The timeline TL6 in FIG. 15(b) can reduce the scan time of the DAP scan SC0 as compared with the reference timeline TL0 by 2·$\Delta T$, so that stress experienced by the subject during a breath-hold can be further mitigated. Moreover, since the start points in time of the scans SCk-SCz in the timeline TL6 are the same as those in the reference timeline TL0, data acquisition can be achieved at times according to the temporal phases.

On the other hand, the timeline TL7 in FIG. 15(c) has longer a scan time of each scan than that in the reference timeline TL0 by $\Delta T$. However, since the start points in time of the scans SCk-SCz in the timeline TL7 are the same as those in the reference timeline TL0, data acquisition can be achieved at times according to the temporal phases.

The preceding description addresses a case in which only the start point in time of the scan SC2 is modified. However, according to the present invention, the start point in time of a scan other than the scan SC2 may be modified (see FIG. 16).

Figure 16:
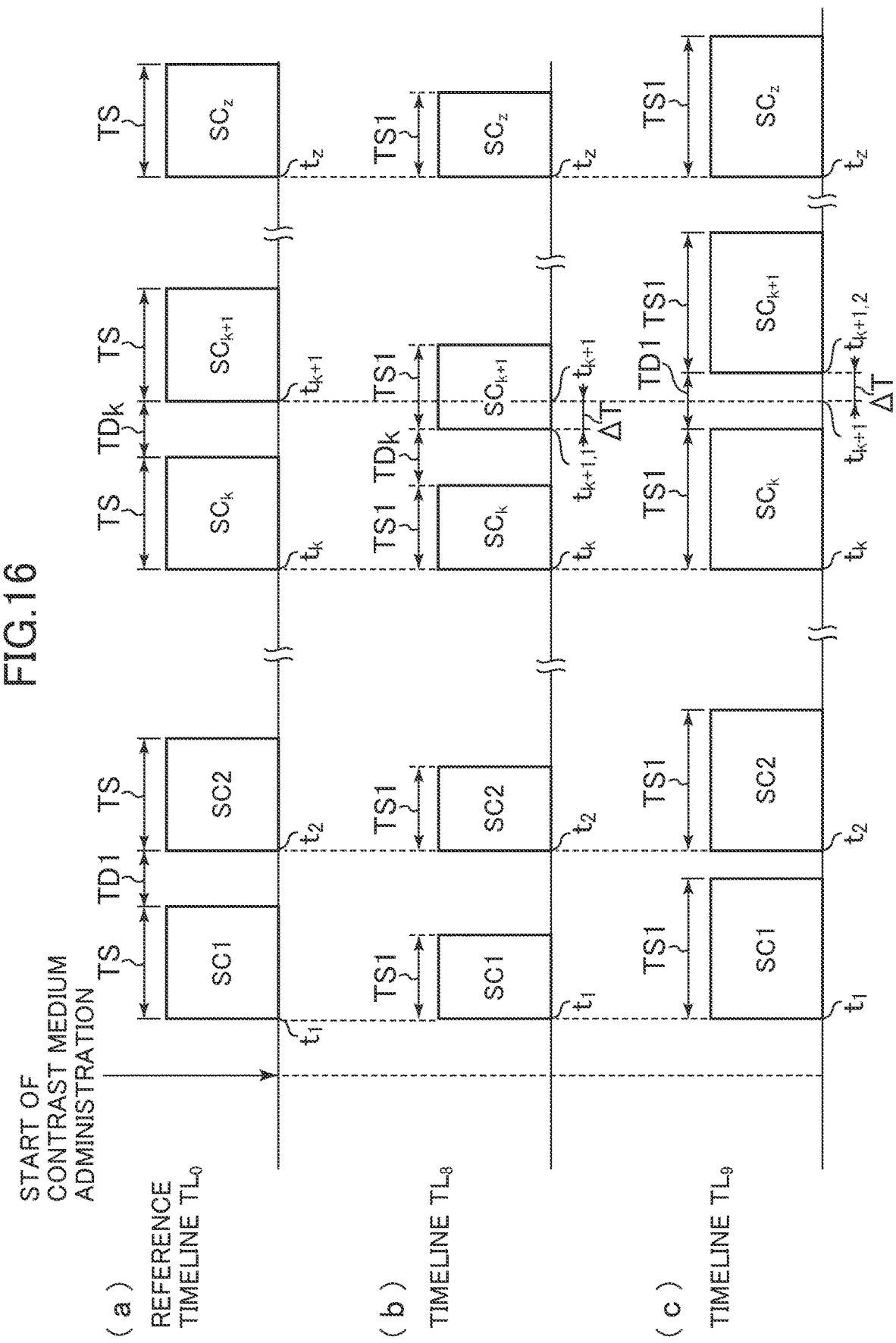
FIG. 16 shows a diagram showing a timeline in which a different delay time is held.

FIG. 16 is a diagram showing a timeline in which the start point in time of a scan other than the scan SC2 is modified.

In a timeline TL8 (see FIG. 16(b)) is shown a case in which the start point in time of a scan $SC_{k+1}$ is modified from $t_{k+1,1}$, while in a timeline TL9 (see FIG. 16(c)) is shown a case in which the start point in time of the scan $SC_{k+1}$ is modified from $t_{k+1}$ to $t_{k+1,2}$. Thus, the start point in time to be modified is not limited to that of the scan SC2, and the start point in time of an arbitrary scan may be modified depending upon the image required in diagnosis.

In the present embodiment, the scan SC1 of the DAP scan SC0 is started at a point in time after a period of time TW1 (see FIG. 3) has elapsed from the start of contrast medium administration. However, the start point in time of the scan SC1 of the DAP scan SC0 may be determined based on a point in time other than that of the start of contrast medium administration depending upon the imaging method. Now imaging methods for determining a start point in time of the scan SC1 based on a point in time other than that of the start of contrast medium administration will be described referring to a Fluoro trigger technique and a Smart prep technique.

FIG. 17 is a diagram explaining the Fluoro trigger technique. In FIG. 17(a), a region RT defined for monitoring a contrast medium is schematically shown. In the Fluoro trigger technique, the region RT for monitoring the contrast medium is defined in a blood vessel, and a scan is started based on a point in time at which a specified amount or more of contrast medium has entered the region RT. In FIG. 17(b), a reference timeline TL0 in conducting the scans SC1-SC4 by the Fluoro trigger technique is schematically shown. The reference timeline TL0 in the Fluoro trigger technique determines the start point in time of the scan SC1 of the DAP scan SC0 as a point in time t1 after a period of time TW0 has elapsed from a point in time t0 at which a specified amount or more of contrast medium has entered the region RT. In FIG. 17(c), a timeline TL10 in conducting the scans SC1-SC4 each having a scan time TS1 is schematically shown. Similarly to the reference timeline TL0, the timeline TL10 determines the start point in time of the scan SC1 of the DAP scan SC0 as a point in time t1 after the period of time TW0 has elapsed from the point in time t0 at which a specified amount or more of contrast medium has entered the region RT.

FIG. 18 is a diagram explaining the Smart prep technique. In FIG. 18(a), a cross-sectional plane S defined for monitoring a contrast medium is schematically shown. In the Smart prep technique, a cross-sectional plane S traversing a blood vessel is defined, and a scan for obtaining an MR image in the cross-sectional plane S is repetitively conducted, which MR image is displayed in the display section in real time. The operator observes the MR image displayed in the display section, and once he/she has decided that a specified amount or more of contrast medium has reached the cross-sectional plane S, he/she operates the operating section 13 (see FIG. 1) to input a command to conduct the scans SC1-SC4. In response to the input, the MR apparatus conducts the scans SC1-SC4. In FIG. 18(b), a reference timeline TL0 in conducting the scans SC1-SC4 in the Smart prep technique is schematically shown. The reference timeline TL0 in the Smart prep technique determines the start point in time of the scan SC1 of the DAP scan SC0 as a point in time $t_{c1}$ after a period of time TW0 has elapsed from the point in time t0 at which the command for conducting the scan is input. In FIG. 18(c), a timeline TL11 in conducting the scans SC1-SC4 each having a scan time TS1 is schematically shown. Similarly to the reference timeline TL0, the timeline TL11 determines the start point in time of the scan SC1 of the DAP scan SC0 as a point in time t1 after the period of time TW0 has elapsed from the point in time t0 at which the command for conducting the scan is input.

Thus, the present invention may be applied to imaging by the Fluoro trigger technique or Smart prep technique.

Moreover, the description of the present embodiment addresses a case in which data in a plurality of temporal phases are acquired by an MR apparatus. The present invention, however, may be applied to a case in which data in a plurality of temporal phases are acquired by a medical apparatus (for example, CT apparatus) other than the MR apparatus.

What is claimed is:

1. A setting apparatus provided in a medical apparatus conducting a first scan for acquiring data in a first temporal phase from a subject to whom a contrast medium is administered, a second scan for acquiring data in a second temporal phase from said subject, and a third scan for acquiring data in a third temporal phase from said subject, said setting apparatus being for setting conditions in conducting said first, second, and third scans, said setting apparatus comprising:

a processor for creating a second timeline based on a first timeline, said first timeline defining a start point in time of said first scan having a first scan time, a start point in time of said second scan, a start point in time of said third scan, and a first delay time from the end of said first scan to the start of said second scan, said second timeline being a timeline in which the scan time of said first scan is modified from said first scan time to a second scan time, wherein said processor sets:

a start point in time of said first scan in said second timeline to the same point in time as that in said first timeline;

a start point in time of said second scan in said second timeline to a point in time delayed relative to the start point in time of said first scan in said second timeline by a sum of said second scan time and said first delay time; and a start point in time of said third scan in said second timeline to the same point in time as that in said first timeline.

2. The setting apparatus as recited in claim 1, wherein said first timeline includes information representing a start point in time at which an output of a first message for asking said subject to hold his/her breath is started and information representing a start point in time at which an output of a second message for allowing said subject to restart breathing is started.

3. The setting apparatus as recited in claim 2, wherein said medical apparatus conducts a fourth scan for acquiring data in a fourth temporal phase from said subject between said second and third scans; and said processor creates said second timeline defining a start point in time of said fourth scan.

4. The setting apparatus as recited in claim 3, wherein a second delay time is placed between said second and fourth scans; and said second message and said first message are output during said second delay time.

5. The setting apparatus as recited in claim 4, wherein a lower limit value of said second delay time is defined as a sum of a length of time of said second message and a length of time of said first message.

6. The setting apparatus as recited in claim 4, wherein a first interval is placed between said first message and said fourth scan; and a lower limit value of said second delay time is defined as a sum of a length of time of said second message, a length of time of said first message, and a length of time of said first interval.

7. The setting apparatus as recited in claim 4, wherein a second interval is placed between said second and first messages; and a lower limit value of said second delay time is defined as a sum of a length of time of said second message, a length of time of said second interval, and a length of time of said first message.

8. The setting apparatus as recited in claim 4, wherein a first interval is placed between said first message and said fourth scan, and a second interval is placed between said second and first messages; and a lower limit value of said second delay time is defined as a sum of a length of time of said second message, a length of time of said second interval, a length of time of said first message, and a length of time of said first interval.

9. The setting apparatus as recited in claim 1, wherein said first and second scans are conducted in a first period of time in which said subject hold his/her breath; and said third scan is conducted in a second period of time in which said subject hold his/her breath.

10. The setting apparatus as recited in claim 9, wherein said first scan is a scan for acquiring data in an early arterial phase, and said second scan is a scan for acquiring data in a late arterial phase.

11. The setting apparatus as recited in claim 1, wherein said second timeline includes information representing a period of time from a point in time at which a specified amount or more of contrast medium has entered a region defined in a blood vessel of said subject to the start point in time of said first scan.

12. The setting apparatus as recited in claim 1, wherein said second timeline includes information representing a period of time from a point in time at which a command for conducting a scan is input to said medical apparatus to the start point in time of said first scan.

13. The setting apparatus as recited in claim 1, wherein said first delay time is set to zero.

* * * * *